(12) United States Patent
Roth et al.

(10) Patent No.: US 7,717,850 B2
(45) Date of Patent: May 18, 2010

(54) SIGNAL PROCESSING FOR ULTRASOUND IMAGING

(75) Inventors: Scott L. Roth, East Hills, NY (US); Harold M. Hastings, Garden City, NY (US)

(73) Assignee: Imacor Inc., Uniondale, NY (US)

( * ) Notice: Subject to any disclaimer, the term of this patent is extended or adjusted under 35 U.S.C. 154(b) by 1076 days.

(21) Appl. No.: 10/997,059

(22) Filed: Nov. 24, 2004

(65) Prior Publication Data

US 2005/0148871 A1   Jul. 7, 2005

Related U.S. Application Data

(60) Provisional application No. 60/525,330, filed on Nov. 26, 2003.

(51) Int. Cl.
*A61B 8/00* (2006.01)
(52) U.S. Cl. .................. 600/437; 600/443; 600/449
(58) Field of Classification Search .............. 600/437, 600/459, 462, 466, 449; 310/322; 345/613, 345/694
See application file for complete search history.

(56) References Cited

U.S. PATENT DOCUMENTS

| | | | |
|---|---|---|---|
| 4,646,748 A | 3/1987 | Fujii et al. |
| 4,771,470 A | 9/1988 | Geiser et al. |
| 4,817,015 A | 3/1989 | Insana et al. |
| 4,977,898 A | 12/1990 | Schwartzschild et al. |
| 4,982,339 A | 1/1991 | Insana et al. |
| RE33,672 E | 8/1991 | Miwa |
| 5,111,823 A | 5/1992 | Cohen |
| 5,224,483 A * | 7/1993 | Lipschutz ............ 600/458 |
| 5,291,893 A | 3/1994 | Slayton |
| 5,325,860 A | 7/1994 | Seward et al. |
| 5,390,676 A | 2/1995 | Katakura |
| 5,409,007 A | 4/1995 | Saunders et al. |
| 5,417,215 A | 5/1995 | Evans et al. |

(Continued)

FOREIGN PATENT DOCUMENTS

EP   0 248 623   12/1987

(Continued)

OTHER PUBLICATIONS

Jérôme Poguet et al., "Phased Array Technology: Concepts, Probes and Applications", NDT.net, (2002), vol. 7, No. 05.

(Continued)

*Primary Examiner*—Ruth S Smith
*Assistant Examiner*—Christopher Cook
(74) *Attorney, Agent, or Firm*—Proskauer

(57) ABSTRACT

The visibility of features in ultrasound images that include at least two types of tissue can be improved by processing the images using a variety of algorithms. In one such algorithm, the ratio of power in a first spatial frequency band to power in a second spatial frequency band is computed for a plurality of samples of a received ultrasound return signal that are associated with a given pixel. In another such algorithm, the ratio of power in a first spatial frequency band to total power is computed. With both algorithms, the computed ratio is then mapped to a gain for the given pixel, the raw intensity of the given pixel is modified in accordance with the gain, and the pixel is displayed with the modified intensity.

36 Claims, 14 Drawing Sheets

U.S. PATENT DOCUMENTS

| | | | |
|---|---|---|---|
| 5,497,777 A | | 3/1996 | Abdel-Malek et al. |
| 5,520,185 A | * | 5/1996 | Soni et al. .................. 600/444 |
| 5,619,998 A | | 4/1997 | Abdel-Malek et al. |
| 5,754,676 A | * | 5/1998 | Komiya et al. .............. 382/132 |
| 5,757,727 A | * | 5/1998 | Hanafy et al. ............... 367/155 |
| 5,839,441 A | | 11/1998 | Steinberg |
| 5,957,846 A | * | 9/1999 | Chiang et al. .............. 600/447 |
| 5,961,464 A | * | 10/1999 | Poland ....................... 600/458 |
| 6,036,645 A | * | 3/2000 | Drost et al. ................. 600/459 |
| 6,059,731 A | * | 5/2000 | Seward et al. .............. 600/459 |
| 6,080,107 A | * | 6/2000 | Poland ....................... 600/458 |
| 6,181,810 B1 | | 1/2001 | Zhang et al. |
| 6,264,609 B1 | | 7/2001 | Herrington et al. |
| 6,359,637 B1 | | 3/2002 | Perkins et al. |
| 6,383,139 B1 | | 5/2002 | Hwang et al. |
| 6,512,854 B1 | | 1/2003 | Mucci |
| 6,514,202 B2 | | 2/2003 | Grunwald |
| 6,533,728 B1 | * | 3/2003 | Belohlavek et al. ......... 600/458 |
| 6,572,547 B2 | | 6/2003 | Miller et al. |
| 6,579,238 B1 | * | 6/2003 | Simopoulos et al. ........ 600/443 |
| 6,679,844 B2 | * | 1/2004 | Loftman et al. ............. 600/443 |
| 6,932,770 B2 | * | 8/2005 | Hastings et al. ............. 600/443 |
| 2001/0029336 A1 | | 10/2001 | Teo |
| 2001/0031924 A1 | | 10/2001 | Seward |
| 2001/0055025 A1 | * | 12/2001 | Deering et al. .............. 345/611 |
| 2003/0092994 A1 | * | 5/2003 | Miller et al. ................ 600/463 |
| 2003/0231790 A1 | * | 12/2003 | Bottema ..................... 382/128 |

FOREIGN PATENT DOCUMENTS

| | | |
|---|---|---|
| EP | 0 749 723 A1 | 12/1996 |
| WO | WO 01/65538 A2 | 9/2001 |

OTHER PUBLICATIONS

Scott L. Roth et al., "Spectral Analysis of Demodulated Ultrasound Returns: Detection of Scatterer Periodicity and Application to Tissue Classification", Ultrasonic Imaging 19. (1997).

Paul A. Heindenreich, "Transesophageal Echocardiography (TEE) in the Critical Care Patient", Transesophageal Echocardiography, vol. 18, No. 4, (2000), pp. 789-805.

K. K. Djoa et al., "Two Decades of Transesophageal Phased Array Probes", Ultrasound in Med. & Biol., vol. 22, No. 1., (1996).

Roy W. Martin et al., "Design characteristics for intravascular ultrasonic catheters," International Journal of Cardiac Imaging 4:201-216, (1989).

Search Report Dated Jul. 11, 2008 from EP 04 75 6114.7.

* cited by examiner

Windows for the Intensity Algorithm and the Frequency Algorithm Along a Scan Line

# SIGNAL PROCESSING FOR ULTRASOUND IMAGING

CROSS REFERENCE TO RELATED APPLICATIONS

This application claims priority to U.S. provisional application No. 60/525,330, filed Nov. 26, 2003.

BACKGROUND

In the medical field, monitoring heart function impacts critical decisions that relate to patient care. One type of prior art heart monitor is the intravascular/intracardiac ultrasound transducer (such as the Accunav™ transducer). This type of transducer, however, is not well suited for transesophageal echocardiography because the transducer elements are oriented longitudinally instead of transversely, which limits the types of images that can be obtained. A second type of prior art heart monitor is the transesophageal echocardiography (TEE) transducer, which is transversely oriented. However, in order to produce repeatedly usable images, the azimuthal aperture of these transducers must be quite large (e.g., 10-15 mm in diameter for adults), which requires a correspondingly large probe. Because of this large probe, conventional TEE often requires anesthesia, can significantly threaten the airway, and is not well suited for long-term monitoring of the heart.

SUMMARY OF THE INVENTION

Transesophageal ultrasound imaging is implemented using a miniature transversely oriented transducer that is preferably small enough to fit in a 7.5 mm diameter probe, and most preferably small enough to fit in a 5 mm diameter probe. Signal processing techniques provide improved depth of penetration, despite the fact that the transducer is so small.

DESCRIPTION OF THE PREFERRED EMBODIMENTS

Figure 1:
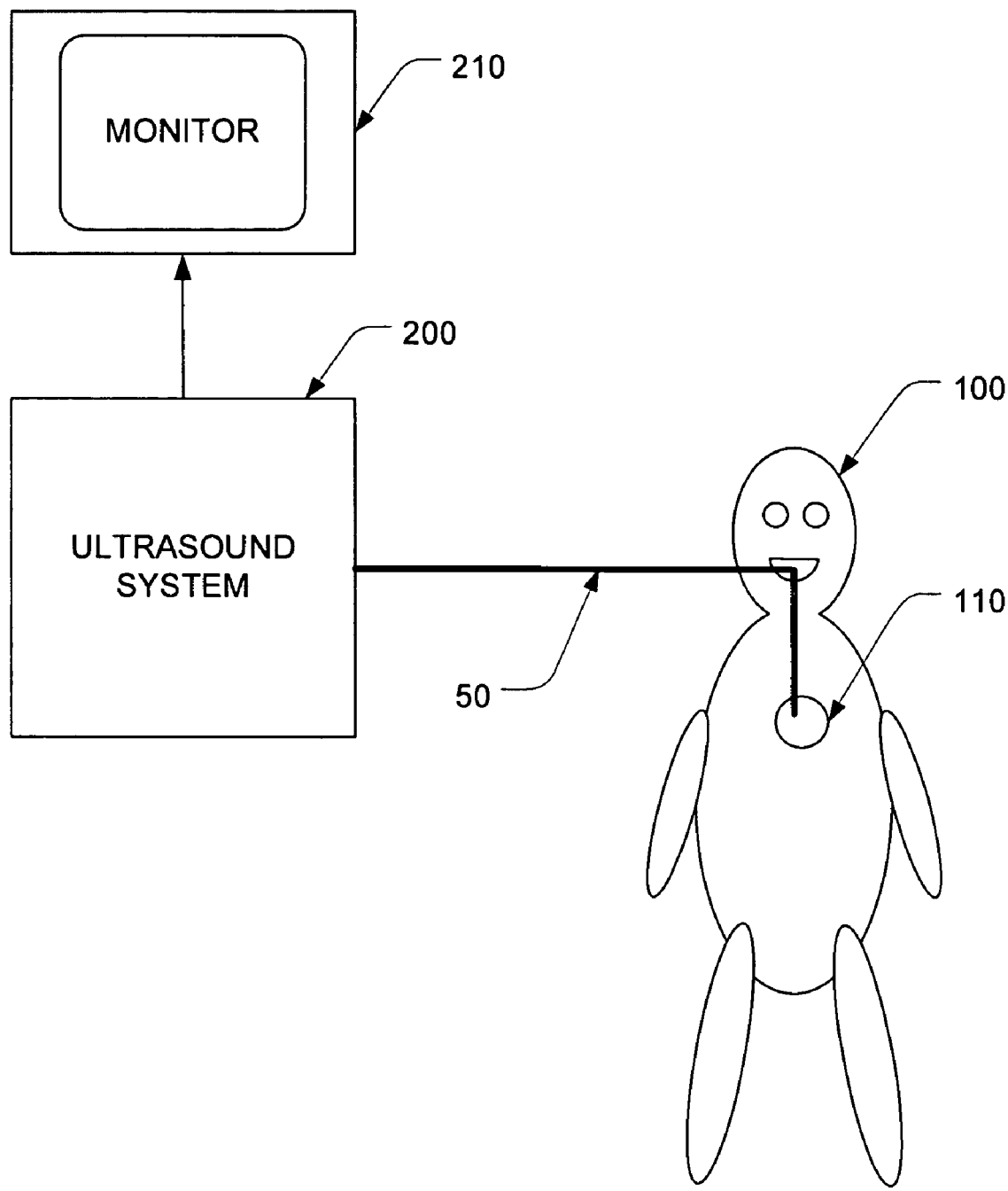
FIG. 1 is an overall block diagram of a system for monitoring cardiac function by direct visualization of the heart.

FIG. 1 is an overall block diagram of a system that may be used for continuous long term monitoring of cardiac function by direct visualization of the heart. An ultrasound system 200 is used to monitor the heart 110 of the patient 100 by sending driving signals into a probe 50 and processing the return signals received from the probe into images, using the image processing algorithms described below. The images generated by those algorithms are then displayed on a monitor 210, in any conventional manner.

Figure 2:
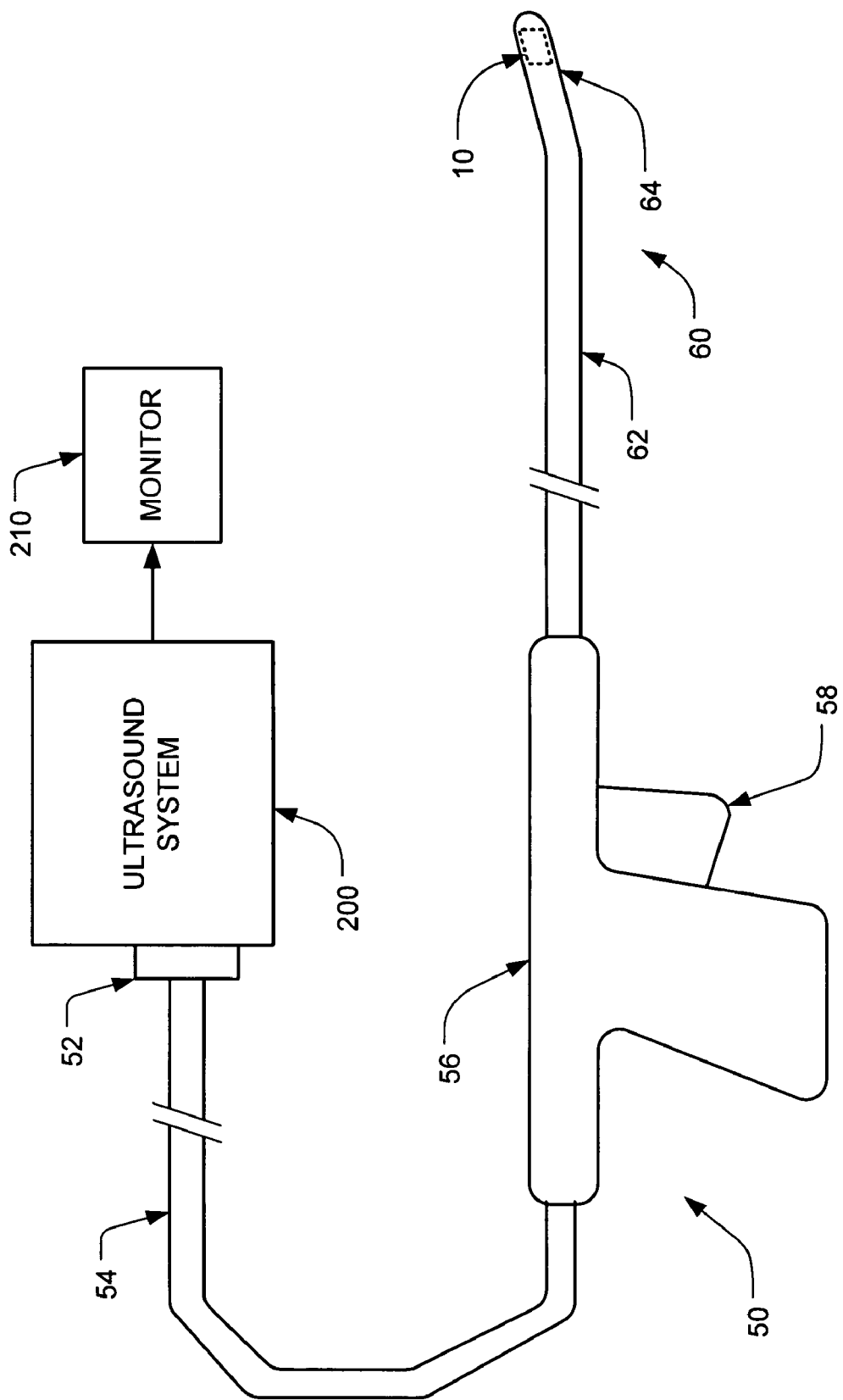
FIG. 2 is a more detailed view of the probe shown in the FIG. 1 embodiment.

FIG. 2 shows more details of the probe 50, which is connected to the ultrasound system 200. At the distal end of the probe 50 there is a housing 60, and the ultrasound transducer 10 is located in the distal end 64 of the housing 60. The next portion is the flexible shaft 62, which is positioned between the distal end 64 and the handle 56. This shaft 62 should be flexible enough so that the distal end 64 can be positioned past the relevant anatomical structures to the desired location, and the handle 56 facilitates the positioning of the distal end 64 by the operator. Optionally, the handle 56 may contain a triggering mechanism 58 which the operator uses to bend the end of the housing 60 to a desired anatomical position as described below.

At the other end of the handle 56 is a cable 54, which terminates, at the proximal end of the probe 50, at connector 52. This connector 52 is used to connect the probe 50 to the ultrasound system 200 so that the ultrasound system 200 can operate the probe. Signals for the ultrasound system 200 that drive the transducer 10 travel through the probe 50 via appropriate wiring and any intermediate circuitry (not shown) to drive the transducer 10, and return signals from the transducer 10 similarly travel back through the probe 50 to the ultrasound system 200 where they are ultimately processed into images. The images are then displayed on the monitor 210 in a manner well known to persons skilled in the relevant art.

In the preferred embodiments, the housing 60 has an outer diameter of less than 7.5 mm. The probe contains the ultrasound transducer 10 and connecting wires, and the housing 60 can be passed through the mouth or nose into the esophagus and stomach.

Figure 3:
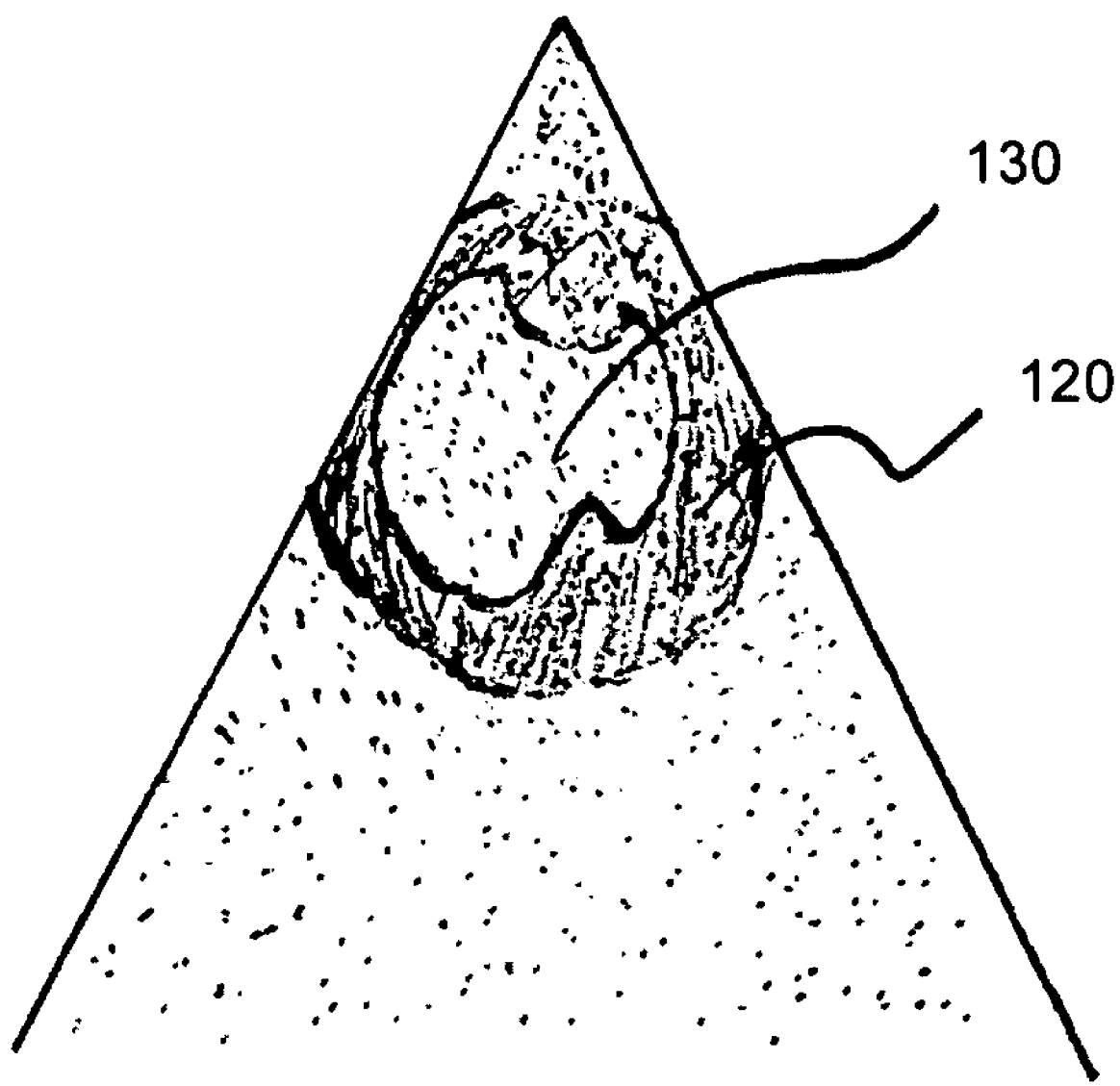
FIG. 3 is a schematic representation of a displayed image of the trans-gastric short axis view (TGSAV) of the left ventricle.

The returned ultrasound signals are processed in the ultrasound system 200 to generate an image of the heart. Preferably, additional signal processing is used to significantly improve image production, as described below. FIG. 3 shows a displayed image of the trans-gastric short axis view (TGSAV) of the left ventricle (LV), which is a preferred view that can be imaged using the preferred embodiments. The illustrated image of the TGSAV appears in a sector format, and it includes the myocardium 120 of the LV which surrounds a region of blood 130 within the LV. The image may be viewed in real time or recorded for later review, analysis, and comparison. Optionally, quantitative analyses of cardiac function may be implemented, including but not limited to chamber and vessel dimensions and volumes, chamber function, blood flow, filling, valvular structure and function, and pericardial pathology.

Unlike conventional TEE systems, the relatively narrow housing used in the preferred embodiments makes it possible to leave the probe in position in the patient for prolonged periods of time.

Figure 4:
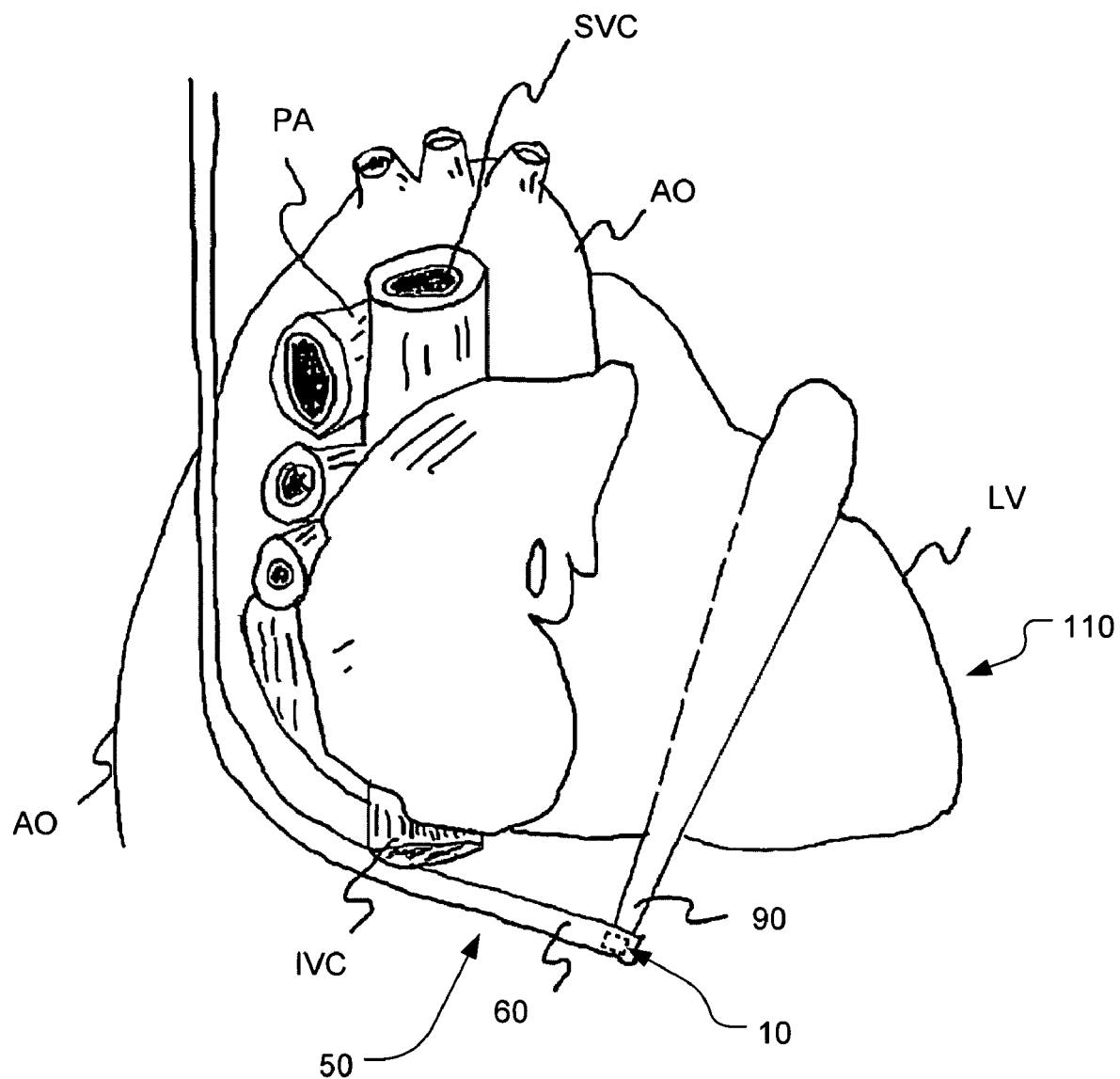
FIG. 4 depicts the positioning of the transducer, with respect to the heart, to obtain the TGSAV.
Figure 5:
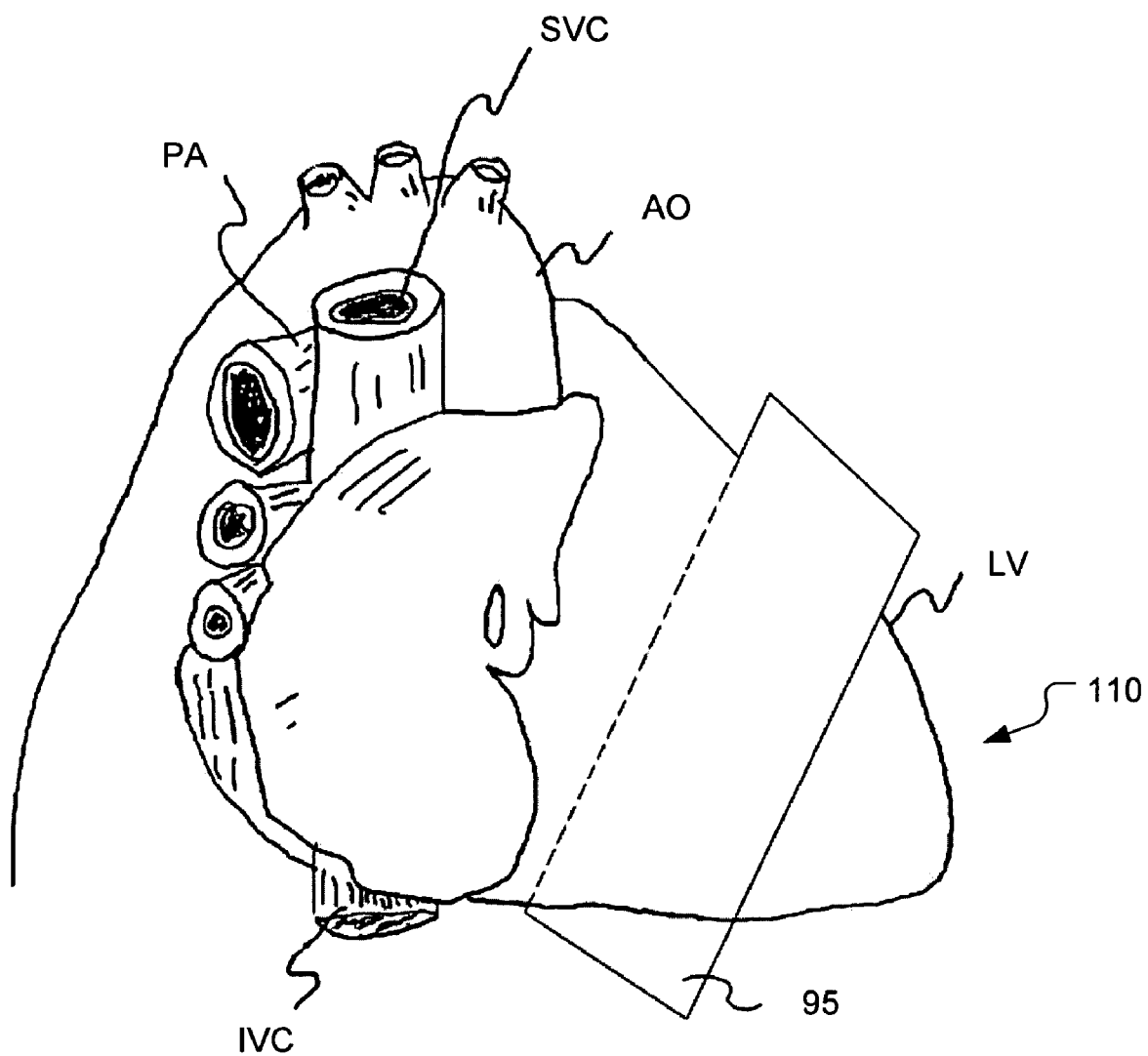
FIG. 5 shows a plane that slices through the trans-gastric short axis of the heart.

As best seen in FIGS. 4 and 5, the probe 50 is used to introduce and position the transducer 10 into a desired location within the patient's body. The orientation of the heart within the chest cavity is such that the apex of the left ventricle is positioned downward and to the left. This orientation results in the inferior (bottom) wall of the left ventricle being positioned just above the left hemidiaphragm, which is just above the fundus of the stomach. During operation, the transducer 10 emits a fan-shaped beam 90. Thus, positioning the transducer 10 in the fundus of the stomach with the fan-shaped beam 90 aimed through the left ventricle up at the heart can provide a trans-gastric short axis view image of the heart 110. The plane of the fan-shaped beam 90 defines the image plane 95 shown in FIG. 5. That view is particularly useful for monitoring the operation of the heart because it enables medical personnel to directly visualize the left ventricle, the main pumping chamber of the heart. Note that in FIGS. 4 and 5, AO represents the Aorta, IVC represents the Inferior Vena Cava, SVC represents the Superior Vena Cava, PA represents the pulmonary artery, and LV represents the left ventricle.

Other transducer positions may also be used to obtain different views of the heart, typically ranging from the mid-esophagus down to the stomach, allowing the operator to directly visualize most of the relevant cardiac anatomy. For example, the transducer 10 may be positioned in the lower esophagus, so as to obtain the conventional four chamber view. Transducer positioning in the esophagus would typically be done without fully flexing the probe tip, prior to advancing further into the stomach. Within the esophagus, desired views of the heart may be obtained by having the operator use a combination of some or all of the following motions with respect to the probe: advance, withdraw, rotate and slight flex.

For use in adults, the outer diameter of the housing 60 is preferably less than about 7.5 mm, more preferably less than about 6 mm, and is most preferably about 5 mm. This is significantly smaller than conventional TEE probes. This size reduction may reduce or eliminate the need for anesthesia, and may help expand the use of TEE for cardiac monitoring beyond its previous specialized, short-term settings. When a 5 mm housing is used, the housing is narrow enough to pass through the nose of the patient, which advantageously eliminates the danger that the patient will accidentally bite through the probe. Alternatively, it may be passed through the mouth like conventional TEE probes. Note that the 5 mm diameter of the housing is similar, for example, to typical NG (naso-gastric) tubes that are currently successfully used long-term without anesthesia in the same anatomical location. It should therefore be possible to leave the probe in place for an hour, two hours, or even six hours or more.

The housing wall is preferably made of the same materials that are used for conventional TEE probe walls, and can therefore withstand gastric secretions. The wiring in the probe that connects the transducer to the rest of the system may be similar to that of conventional TEE probes (adjusted, of course, for the number of elements). The housing is preferably steerable so that it can be inserted in a relatively straight position, and subsequently bent into the proper position after it enters the stomach. The probe tip may be deflected by various mechanisms including but not limited to steering or pull wires. In alternative embodiments, the probe may use an intrinsic deflecting mechanism such as a preformed element including but not limited to pre-shaped materials. Optionally, the probe (including the transducer housed therein) may be disposable.

For imaging the TGSAV of the LV, the probe tip is preferably ultimately "ante-flexed" (flexed towards the front of the patient) approx. 70-110 degrees. This may be implemented, for example, by building a triggerable ante-flex (e.g., on the order of 70 degrees) into the probe through a combination of a pre-formed element, a device to prevent flexing during insertion and a trigger to release the preformed element from the insertion limit once the probe is in the desired anatomic location. Optionally, a pull-wire may be used for steering to provide the additional 0-40 degrees of flex after the transducer is lowered to the appropriate depth. The triggerable ante-flex component is preferably designed so that it will present little resistance to returning to the unflexed position during probe removal.

Figure 6A:
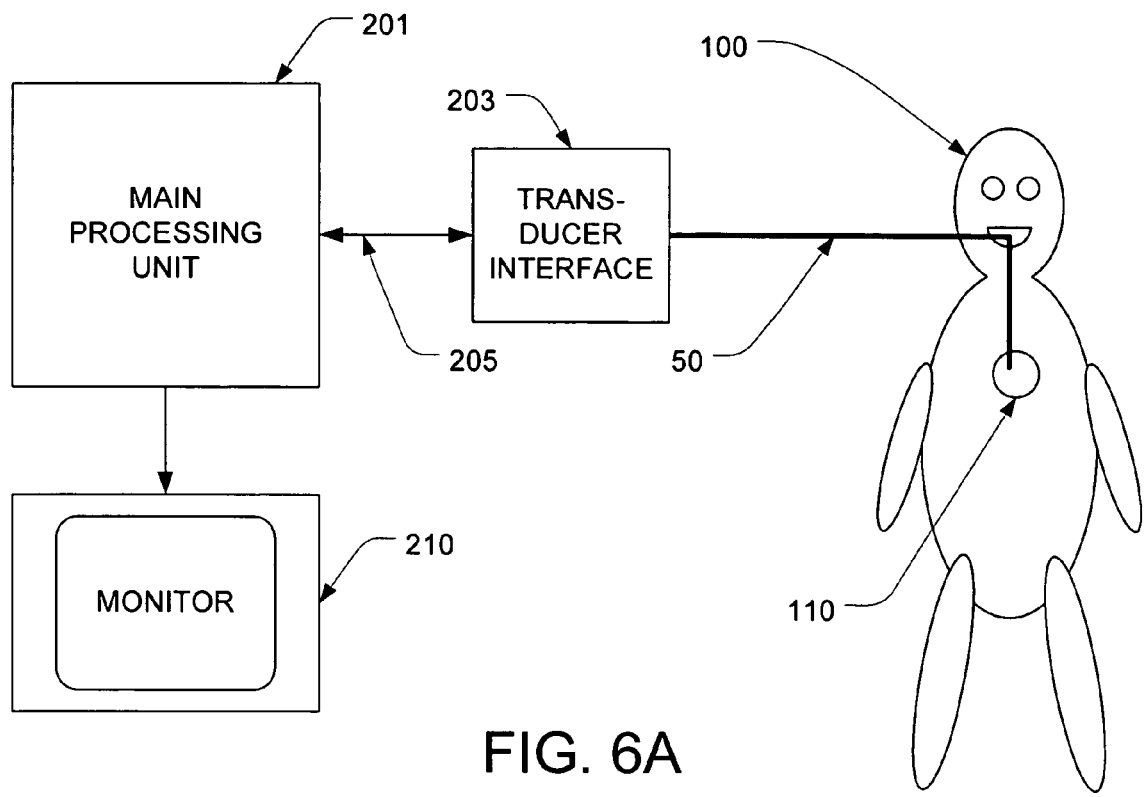
FIG. 6A shows an optional probe interface configuration.

FIG. 6A shows an optional configuration that is similar to the FIG. 1 embodiment, except that the circuitry that interfaces with the probe 50 is relocated to an interface box 203. The rest of the ultrasound system remains in the main processing unit 201, which communicates with the interface box 203 via an appropriate cable 205. The interface box 203 contains circuitry to amplify the signals from the transducer 10 and/or digitize those signals. Using such an interface box advantageously provides shorter signal paths for those parts of the circuit that are most sensitive to electrical noise (i.e., where the signals are small). The transmit signals that drive the transducer 10 may also be generated within the interface box 203 if desired.

Figure 6B:
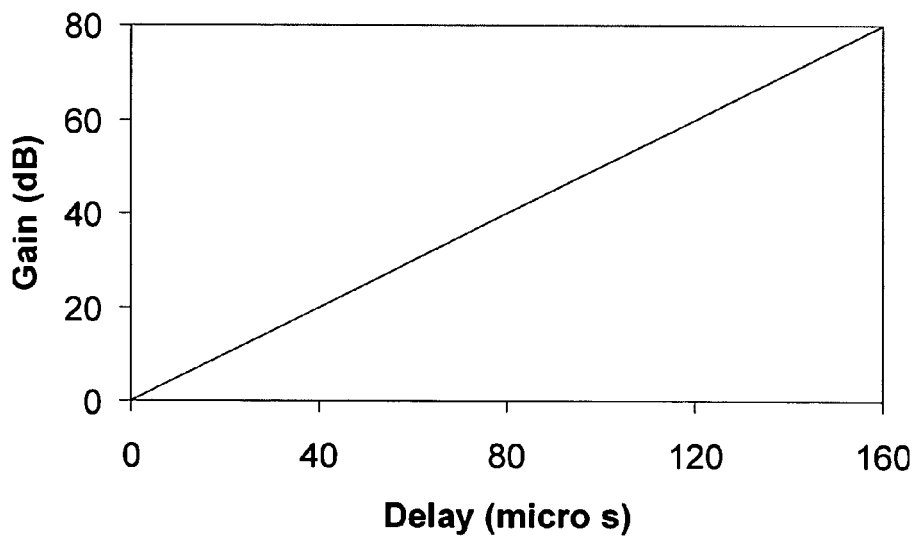
FIG. 6B is a graph of gain characteristics for a TGC amplifier.

Electrical noise may be further reduced using a variety of techniques. For example, in one embodiment, the interface box 203 houses a preamplifier that serves as the first stage in the amplification/processing chain, and separate power supplies are used for the interface box and the main processing unit 201 to reduce electronic noise pass-through. In another embodiment, the interface box 203 houses a preamplifier that serves as the first stage in the amplification/processing chain, and the preamplifier operates on battery power. For both of these embodiments, time gain compensation (TGC) is preferably implemented in that preamplifier. TGC compensates for the fact that the return signals from distant scatterers are weaker than those for nearby scatterers by increasing the gain for signals with longer travel time. TGC may be implemented using conventional techniques that are well known to persons skilled in the relevant art. An example of suitable gain vs. delay characteristics for TGC is shown in FIG. 6B, where the x-axis represents the delay between transmission of the ultrasound pulse and detection of the return signal, and corresponds to depth as follows:

Depth(in cm)=0.077 cm/μs×delay(in μs).

Implementing TGC in the preamplifier facilitates efficient digitization. The preamplifier may also provide amplitude compandoring (a form of compression) to further facilitate efficient digitization. Optionally, the preamplifier's output may be digitized in the interface box, in which case only digital signals would be sent from the interface box to the main processing unit to further reduce electrical noise. These digital signals may even be opto-isolated to eliminate all possible electrical connections in the return path, to reduce electrical noise pass-through further still.

Figure 7A:
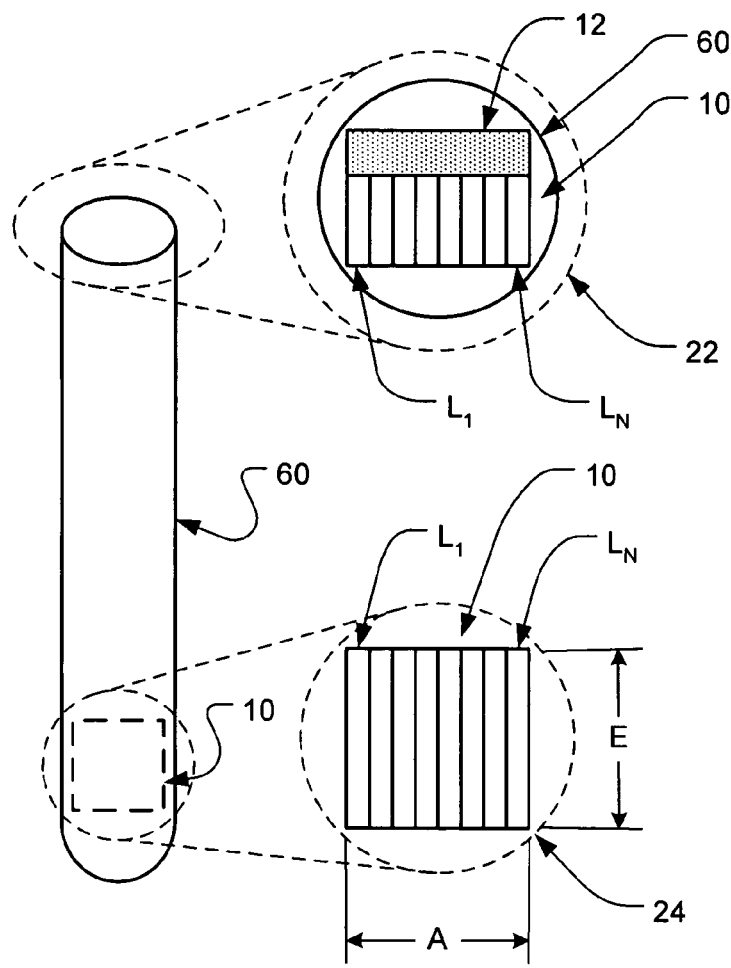
FIGS. 7A, 7B, and 7C show a first preferred transducer configuration.
Figure 7B:
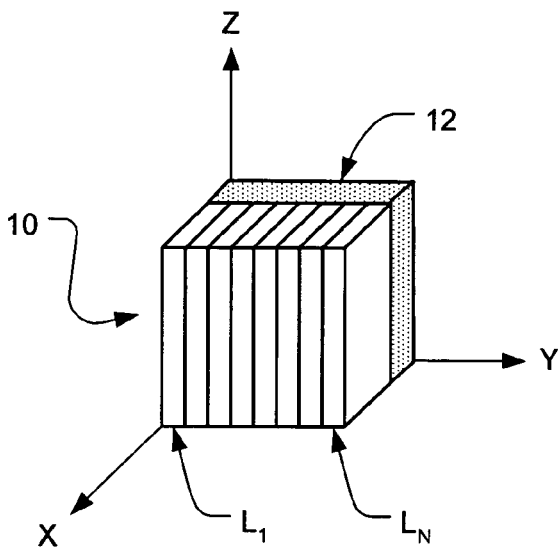
Figure 7C:
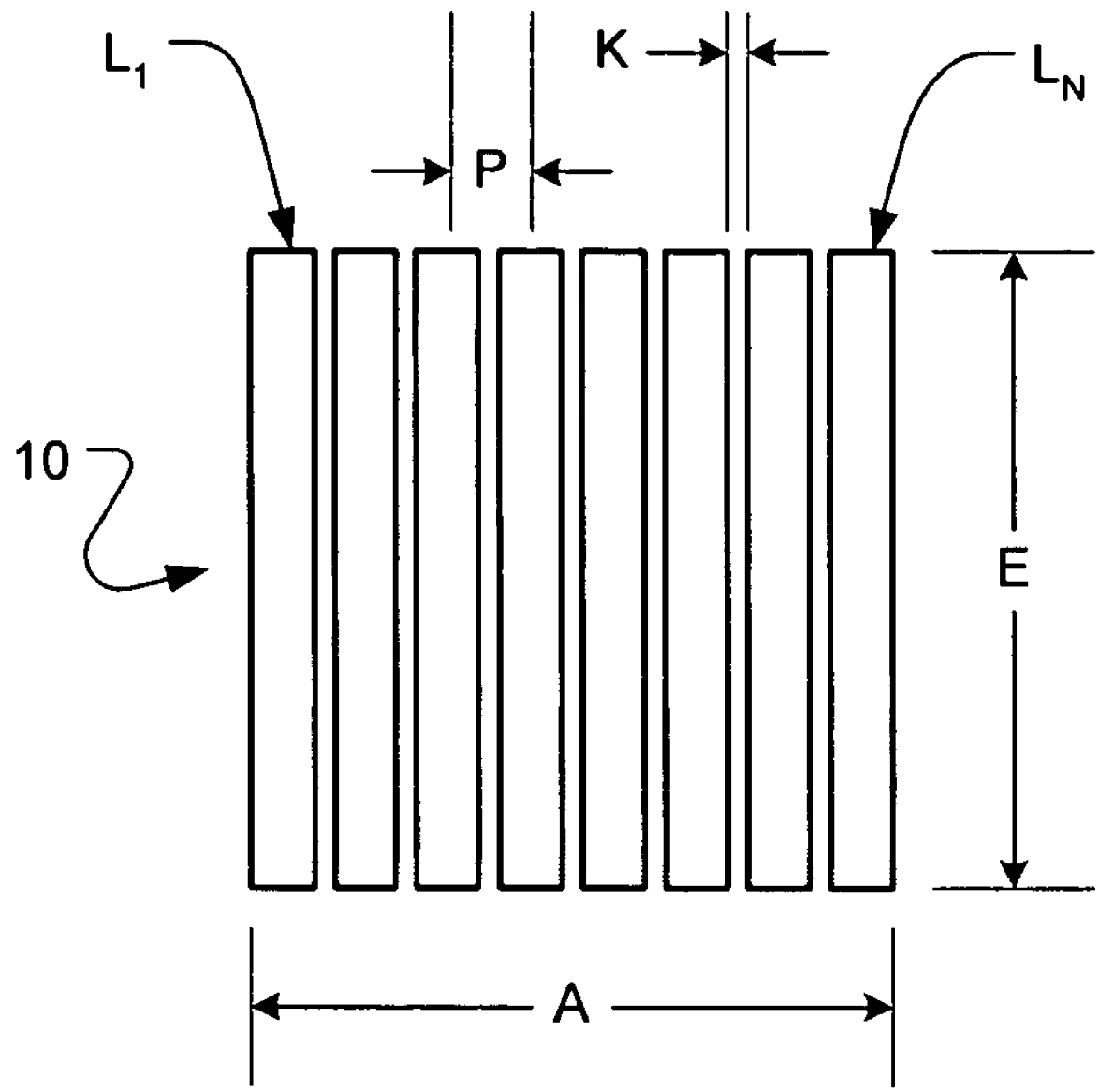

The preferred embodiments described herein provide a good quality image of the TGSAV of the LV from a transducer that is small enough to fit in the narrow housing described above. FIGS. 7A-7C depict a first preferred transducer 10. FIG. 7A shows the location of the transducer 10 in the distal end of the housing 60, and also includes a top view 22 of the transducer 10 surrounded by the wall of the housing 60 and a front cutaway view 24 of the transducer 10.

As best seen in FIG. 7B, the azimuth axis (Y axis) is horizontal, the elevation axis (Z axis) is vertical, and the X axis projects out of the page towards the reader. When steered straight forward by energizing the appropriate elements in the transducer, the beam will go straight out along the X axis. The steering signals can also send the beam out at angles with respect to the X axis, in a manner well know to persons skilled in the relevant arts.

The transducer 10 is preferably a phased array transducer made of a stack of N piezo elements $L_1 \ldots L_N$, an acoustic backing 12, and a matching layer in the front (not shown), in a manner well known to those skilled in the relevant art. As understood by persons skilled in the relevant arts, the elements of phased array transducers can preferably be driven individually and independently, without generating excessive vibration in nearby elements due to acoustic or electrical coupling. In addition, the performance of each element is preferably as uniform as possible to help form a more homogeneous beam. Optionally, apodization may be incorporated into the transducer (i.e., tapering the power driving transducer elements from a maximum at the middle to a minimum near the ends in the azimuthal direction, and similarly tapering the receive gain).

The preferred transducers use the same basic operating principles as conventional TEE transducers to transmit a beam of acoustic energy into the patient and to receive the return signal. However, while the first preferred transducer 10 shown in FIGS. 7A-7C shares many characteristics with conventional TEE transducers, the first preferred transducer 10 differs from conventional transducers in the following ways:

TABLE 1

| Feature | conventional TEE transducer | first preferred transducer |
| --- | --- | --- |
| Size in the transverse (azimuthal) direction | 10-15 mm | about 4-5 mm |
| Number of elements | 64 | about 32-40 |
| Size in the elevation direction | 2 mm | about 4-5 mm |
| Front face aspect ratio (elevation:transverse) | about 1:5 | about 1:1 |
| Operating frequency | 5 MHz | about 6-7.2 MHz |

In FIG. 7A, the elevation is labeled E and the transverse aperture is labeled A on the front cutaway view 24 of the transducer 10. The location of the wall of the housing 60 with respect to the transducer 10 can be seen in the top view 22.

FIG. 7C shows more details of the first preferred transducer 10. Note that although only eight elements are shown in all the figures, the preferred transducer actually has between about 32-40 elements, spaced at a pitch P on the order of 130 µm. Two particularly preferred pitches are approximately 125 µm (which is convenient for manufacturing purposes) and approximately 128 µm (0.6 wavelength at 7.2 MHz). When 32-40 elements are spaced at a 125 µm pitch, the resulting azimuth aperture A (sometimes simply called the aperture) of the transducer 10 will be between 4 and 5 mm. The reduced element count advantageously reduces the wire count (compared to conventional TEE transducers), which makes it easier to fit all the required wires into the narrower housing. The kerf K (i.e., the spacing between the elements) is preferably as small as practical (e.g., about 25-30 µm or less). Alternative preferred transducers may have between about 24-48 elements, spaced at a pitch between about 100-150 µm.

Figures 8A, 8B:
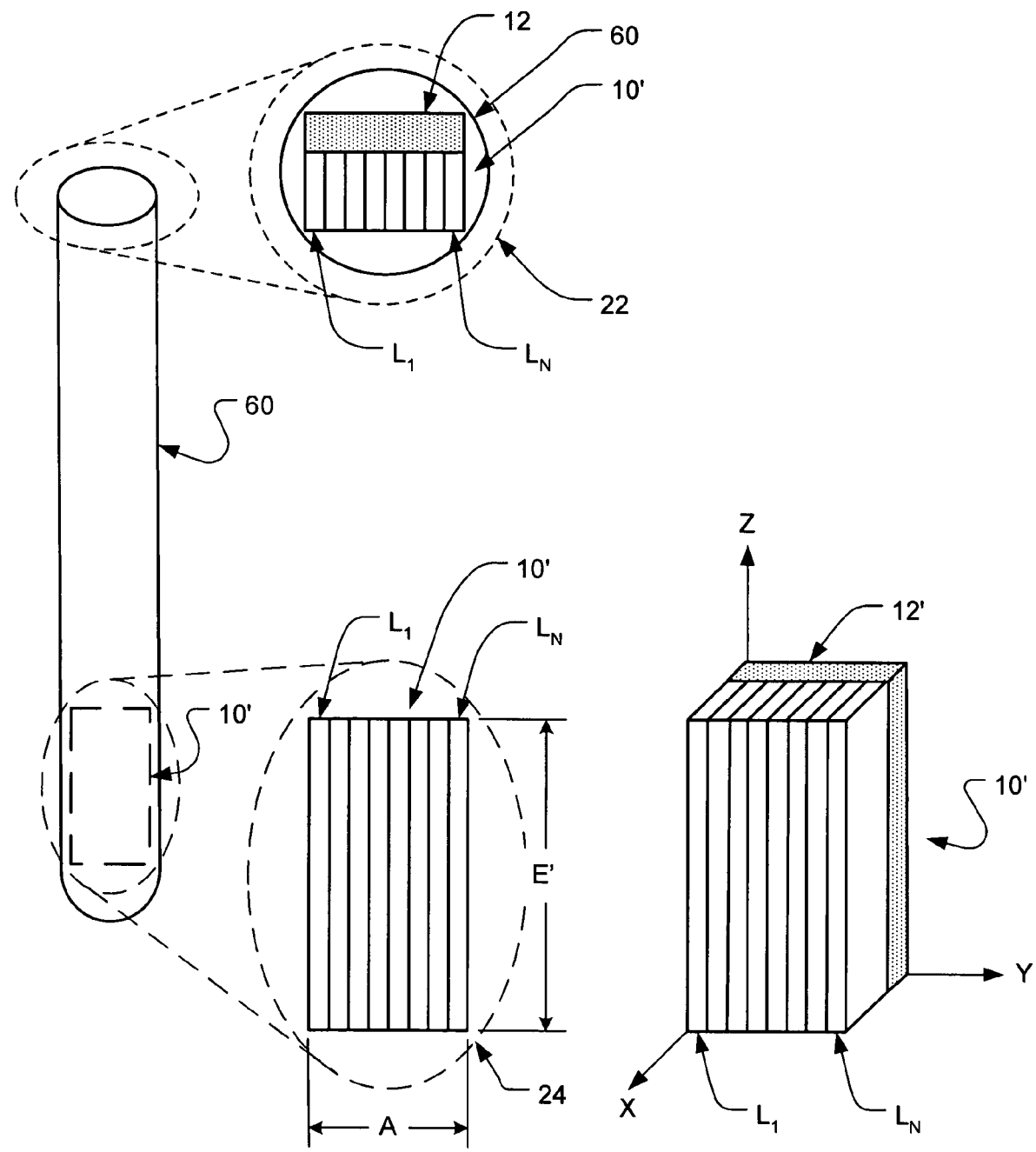
FIGS. 8A and 8B show a second preferred transducer configuration.

A second preferred transducer 10' is shown in FIGS. 8A-8B. This transducer 10' is similar to the first preferred transducer 10 described above in connection with FIGS. 7A-7C, except it is taller in the elevation direction. Similar reference numbers are used in both sets of figures to refer to corresponding features for both transducers. Numerically, the second transducer differs from conventional transducers in the following ways:

TABLE 2

| Feature | conventional TEE transducer | second preferred transducer |
| --- | --- | --- |
| Size in the transverse (azimuthal) direction | 10-15 mm | about 4-5 mm |
| Number of elements | 64 | about 32-40 |
| Size in the elevation direction | 2 mm | about 8-10 mm |
| Front face aspect ratio (elevation:transverse) | about 1:5 | about 2:1 |
| Operating frequency | 5 MHz | about 6-7.2 MHz |

In alternative embodiments, the transducer 10 may be built with a size in the elevation direction that lies between the first and second preferred transducers. For example, it may have a size in the elevation direction of about 7.5 mm, and a corresponding elevation:transverse aspect ratio of about 1.5:1.

The transducer 10 preferably has the same transverse orientation (with respect to the axis of the housing 60) as conventional TEE transducers. When the transducer is positioned in the stomach (as shown in FIG. 4), the image plane (azimuthal/radial plane) generated by the transducer intersects the heart in the conventional short axis cross-section), providing the trans-gastric short axis view of the heart, as shown in FIGS. 3 and 5. The transducer is preferably as wide as possible in the transverse direction within the confines of the housing. Referring now to the top view 22 in FIG. 7A, two examples of transducers that will fit within a 5 mm housing are provided in the following table, along with a third example that fits in a housing that is slightly larger than 5 mm:

TABLE 3

| Parameter | first example | second example | third example |
| --- | --- | --- | --- |
| number of elements in the transducer | 38 | 36 | 40 |
| a (azimuthal aperture) | 4.75 mm | 4.50 mm | 5.00 mm |
| b (thickness) | 1.25 mm | 2.00 mm | 2.00 mm |
| c (inner diameter of housing at the transducer) | 4.91 mm | 4.92 mm | 5.39 mm |
| housing wall thickness | 0.04 mm | 0.04 mm | 0.04 mm |
| outer diameter of housing | 4.99 mm | 5.00 mm | 5.47 mm |

Referring now to the top view 22 in FIG. 8A, the three examples in Table 3 are also applicable for fitting the second preferred transducer 10' within a 5-5.5 mm housing.

The above-describe embodiments assume that the housing is round. However, other shaped housings may also be used to house the transducer, including but not limited to ellipses, ovals, etc. In such cases, references to the diameter of the housing, as used herein, would refer to the diameter of the smallest circle that can circumscribe the housing. To account for such variations in shape, the housing may be specified by its outer perimeter. For example, a 5 mm round housing would have a perimeter of 5π mm (i.e., about 16 mm). When a rectangular transducer is involved, using an oval or elliptical housing can reduce the outer perimeter of the housing as compared to a round housing. For example, an oval that is bounded by a 6 mm×2 mm rectangle with its corners rounded to a radius of 0.5 mm contains a 5 mm×2 mm rectangular region, which can hold the third example transducer in Table 3. Allowing for a 0.04 mm housing wall thickness yields an outer perimeter of 15.4 mm, which is the same outer perimeter as a 4.9 mm diameter circle. The following table gives the outer perimeters that correspond to some of the diameters discussed herein:

TABLE 4

| outer diameter | outer perimeter |
|---|---|
| 2.5 mm | 8 mm |
| 4 | 13 |
| 5 | 16 |
| 6 | 19 |
| 7.5 | 24 |

Since the characteristics of the last one or two elements at each end of the transducer may differ from the characteristics of the remaining elements (due to differences in their surroundings), the last two elements on each side may be "dummy" elements. In such a case, the number of active elements that are driven and used to receive would be the total number of element (shown in Table 3) minus four. Optionally, the wires to these dummy elements may be omitted, since no signals need to travel to or from the dummy elements. Alternatively, the wires to may be included and the last two elements may be driven, with the receive gain for those elements severely apodized to compensate in part for their position at the ends of the transducer.

Preferably, conventional beam-forming techniques are used to generate and aim a beam of acoustic energy in the desired directions. For example, focusing in the azimuthal direction may be accomplished by phasing (i.e., timing the excitation of individual elements $L_1 \ldots L_N$ in the array, and using appropriate time delays in the returns of individual elements before summing the respective returns into an ultrasound return signal). Focusing in the elevation direction may be accomplished based on the near-field and far-field properties of the sound signal, and will depend upon the physical height of the elements in the elevation direction and optional acoustic lenses.

Figure 9:
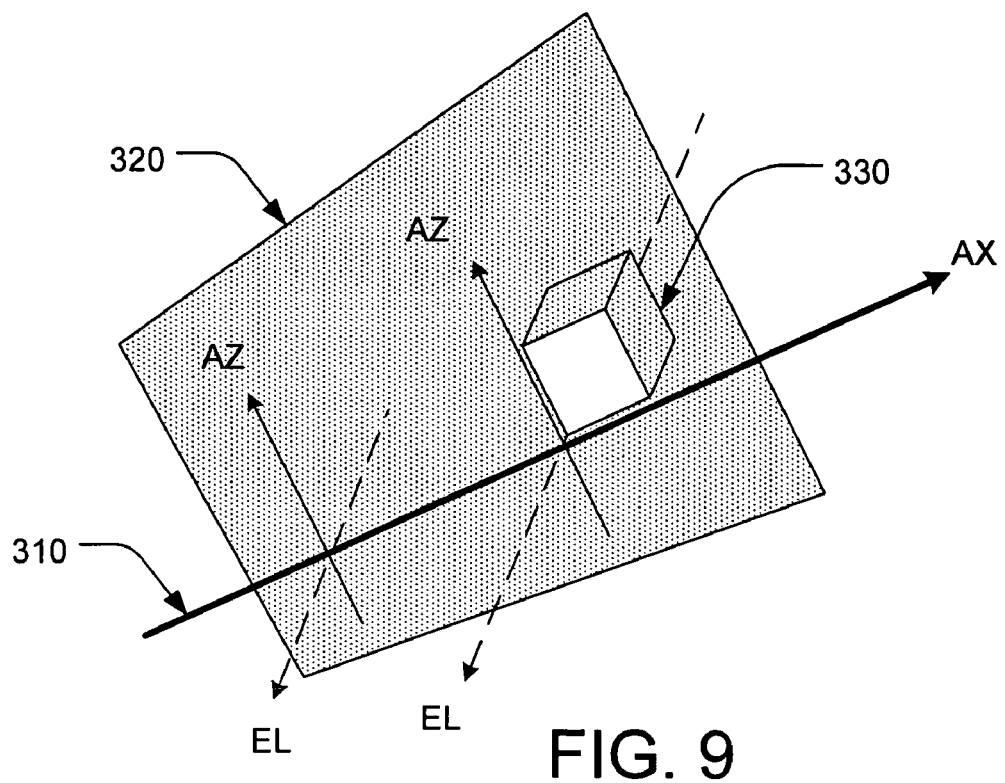
FIG. 9 shows the components of spatial resolution.

Resolution adequate to determine LV size and function depends upon a combination of resolution in azimuth, elevation, and axis. This combination is referred to as "spatial resolution" and is illustrated in FIG. 9. FIG. 9 shows the image plane 320 and a scan line 310 that lies on the image plane 320. The axial direction AX is defined by the scan lines 310, and the transducer (not shown) is located far back along the AX axis. Out at the voxels being imaged, the azimuthal direction AZ is perpendicular to the AX axis within the image plane 320, and the elevation axis EL is perpendicular to the image plane 320. In an ideal system, each voxel would be a point. In real-world systems, however, the voxels have a volume that is defined by the resolution in all three directions AX, AZ and EL, as shown for voxel 330. Similarly, while the image plane 320 is depicted as a thin plane, the real-world image plane will have a thickness in the elevation direction EL that is equal to the thickness of the voxel 330 in the elevation direction.

The general formula for azimuthal and elevation resolutions is:

$$\Delta\theta \approx 1.22 \lambda/d,$$

where $\Delta\theta$ denotes the beamwidth in radians, $\lambda$ the wavelength (corresponding to the transducer center frequency) and d the aperture in the given direction (azimuth or elevation). The wavelength $\lambda$ and aperture d are measured in the same units (e.g., μm).

Axial resolution depends indirectly upon the wavelength $\lambda$. Although the inventors are not aware of any specific formula for axial resolution, it is typically on the order of 16-64 times the wavelength. Thus, increasing the center frequency increases all three components of spatial resolution. A center frequency on the order of 5-10 MHz is high enough to provide adequate resolution.

Figure 10:
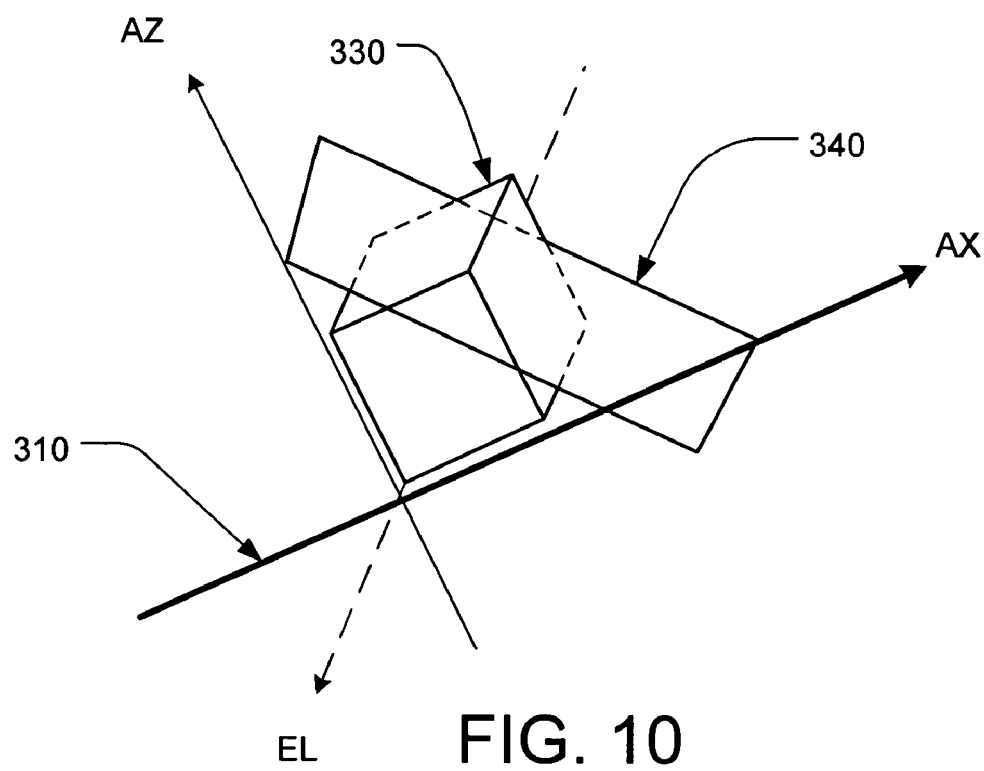
FIG. 10 shows the interaction between the shape of the resolution voxel and the boundary.

FIG. 10 illustrates the interplay between the three components in determining the interaction between the shape of the resolution voxel and the boundary orientation in detecting and determining boundaries. It shows the same voxel 330 that appears in FIG. 9, and also shows an illustrative piece 340 of the boundary being imaged that coincides with that voxel. If the boundary orientation is random with respect to the resolution voxel, one suitable approach is to make the resolution voxel as cubical as possible. In order to obtain that shape, the azimuth and elevation resolutions for a given voxel should be approximately equal, which occurs when the front face of the transducer is approximately square, as it is for the first preferred transducer discussed above in connection with FIGS. 7A-7C.

For the first preferred transducer, the elevation aperture is approximately the same as the azimuth aperture. In other words, the front face of the transducer has a elevation:transverse aspect ratio that is approximately 1:1 (i.e., it is approximately square). A square transducer with a width of 4-5 mm in the transverse direction would therefore have an area of approximately 16-25 mm$^2$.

The formulas for azimuthal and elevation resolution are:

$$\Delta\theta_{AZ} = 1.22 \times d_{AZ}$$

and $$\Delta\theta_{EL} = 1.22 \times \lambda/d_{EL}$$

where $\Delta\theta_{AZ}$ and $\Delta\theta_{EL}$ are the azimuth and elevation resolutions, respectively, (both measured in radians); and $d_{AZ}$ and $d_{EL}$ are the azimuth and elevation apertures, respectively. These components may be combined into a single equation for overall resolution as a function of area and frequency, as follows:

$$\Delta\theta_{OVERALL} = 1.5 \times \lambda^2/(d_{AZ} \times d_{EL})$$

As explained above, increasing the center frequency results in increased resolution. However, increasing the center frequency also reduces the penetration depth due to frequency-dependent attenuation, which is governed by the approximate formula $$a \approx 0.5 f \times r$$

where a denotes the one-way attenuation in dB, f is the center frequency in MHz, and r the depth in cm. Thus, one-way frequency dependent attenuation will typically be about 0.5 dB MHz$^{-1}$ cm$^{-1}$ and typical round-trip frequency dependent attenuation will typically be about 1 dB MHz$^{-1}$ cm$^{-1}$.

The inventors have determined that a transducer center frequency between about 6 and 7.2 MHz provides a good trade-off between resolution and depth of penetration for TEE using a transducer with a 4.75 mm azimuthal aperture. In the embodiments described herein, that range of frequencies can typically provide enough depth of penetration to image the far wall of the left ventricle (in the TGSAV) so that the interior volume of the left ventricle can be computed. (In most subjects, a 12 cm depth of penetration is adequate to image the far wall. For many subjects, a depth of penetration of about 9-10 cm will suffice).

When the transducer elements are spaced at a 125 µm pitch, using a transducer center frequency of 6.16 MHz is particularly advantageous because it corresponds to a wavelength of $\lambda$=250 µm. At that wavelength, the elements are spaced at a pitch of 0.5$\lambda$, which is sometimes referred to as "half-wavelength pitch". As is well known to those skilled in the art, a half-wavelength pitch is excellent for eliminating grating lobes while still minimizing element count for a given azimuth aperture. Somewhat larger pitches, e.g. 0.6$\lambda$, still work reasonably well in terms of eliminating grating lobes. Thus, for transducers that can operate at a range of center frequencies, acceptable performance can be maintained even if the frequency is increased about 20% (i.e., to the point where the pitch becomes about 0.6$\lambda$).

As explained above, the formula for the angular resolution is $\theta \approx \lambda/d$. Referring to the tables above, the first example of the first preferred transducer has a 38 element transducer with a 125 µm pitch, resulting in a 4.75 mm transducer width (d=4750 µm). It is preferably approximately square and operates at a center frequency of 6.16 MHz ($\lambda$=250 µm). When those values for d and $\lambda$ are plugged into the equation for resolution, the result is $\theta \approx 0.053$ radians, which converts to approximately 3 degrees resolution in both azimuth and elevation.

The increased size of the transducer in the elevation direction helps improve the angular resolution of the system in the elevation direction (as compared to a conventional TEE transducer with a 2 mm elevation). This increased resolution in the elevation direction helps compensate for losses in angular resolution in the azimuth direction caused by shrinking the azimuthal aperture down to about 4-5 mm.

The inventors have noticed that increasing the size of the transducer in the elevation direction further, so that it is larger than the size in the azimuthal direction provides improved performance when imaging the far wall of the heart in the TGSAV. This increase in transducer elevation causes the resolution voxel to shrink in the elevation direction at distances that correspond to the far wall of the LV, which results in increased resolution in the elevation direction. The inventors believe that increasing resolution in this direction is helpful at least in part because the far wall is slanted about the Y axis with respect to the front face of the transducers. (The Y axis is shown in FIG. 8B.) Shrinking the size of the voxel in the elevation direction therefore minimizes the variations of the components of return signals arising from specular reflections that fall within a single voxel.

The inventors have determined that the images of the TGSAV are better when the transducer is more than 1.5 times as large in the elevation direction as the transverse direction, and that the best images of the TGSAV are obtained when the transducer is about two times as large in the elevation direction as the transverse direction, as it is for the second preferred transducer 10' described above in connection with FIGS. 8A and 8B and Table 2.

Figure 11:
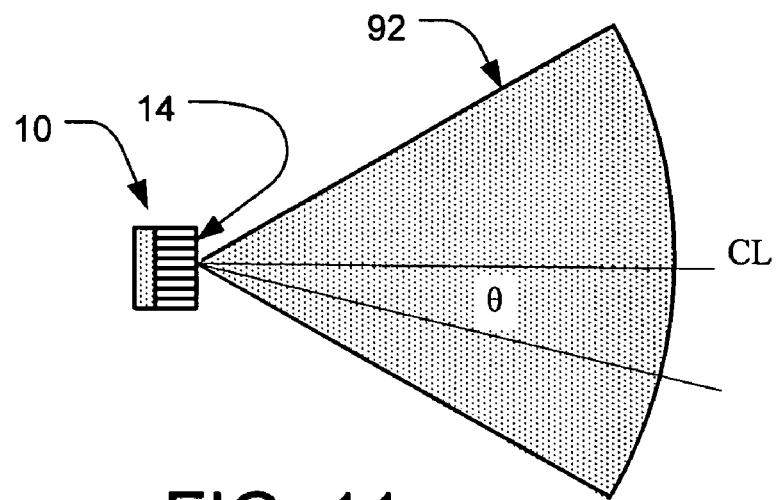
FIG. 11 shows the sector width.

Instead of the 90° sector width that is typically used in conventional TEE systems, the preferred embodiment uses a smaller sector width (e.g., 60 degrees). Referring now to FIG. 11, a 60° sector 92 is shown emanating from the front face 14 of the transducer 10. The effective azimuthal aperture at an angle $\theta$ from the centerline CL can be obtained by multiplying the (nominal) azimuthal aperture (at $\theta$=0) by cos($\theta$). Since cos(30°)=0.866 and cos(45°)=0.707, restricting the sector width to 60° (i.e., 30° on each side of the center line CL) causes a smaller degradation in worst-case azimuthal aperture: azimuthal aperture is degraded by only 13.4%, compared with 26.8% in the case of a 90° sector width. For example, the worst case aperture for a 4.75 mm wide transducer (5 mm housing diameter) in a 60° sector would be about 4.11 mm. The result is improved effective azimuthal aperture, which improves the overall resolution obtainable with small transducers. If a conventional 90° sector were to be used, a 5.82 mm wide transducer (6.1 mm housing diameter) would be needed in order to provide the same worst case aperture.

Figure 12:
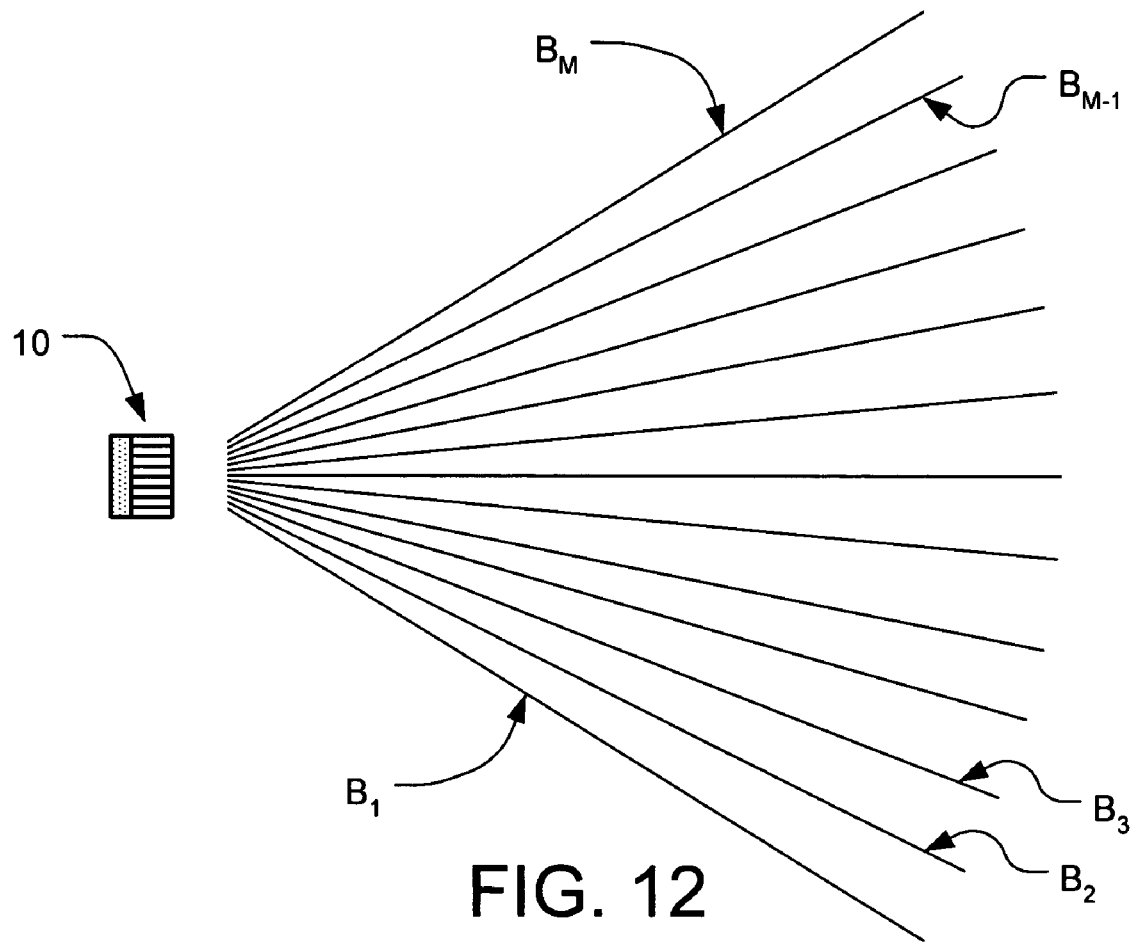
FIG. 12 is a schematic illustration of the paths of the ultrasound beam as it is swept through the sector.

After a beam of ultrasound energy is sent into the patient using the transducer described above, the ultrasound return signal is received, preferably by the same transducer. The transducer converts the ultrasound return signal into an electrical return signal. This process continues as the beam is swept through the imaging sector. FIG. 12 is a schematic illustration of the path of the ultrasound beam as it is swept through the sector, first along line $B_1$, then along line $B_2$, and continuing on through line $B_M$. These scan lines $B_1 \ldots B_M$ correspond to the fan-shaped beam 90 (shown in FIG. 4) and the sector 92 (shown in FIG. 11). Although the illustration only includes a small number (M) of scan lines, an actual system would have many more scan lines that are much more densely packed, so as not to adversely impact the azimuthal resolution.

The electrical return signal can be modeled as being an amplitude-modulated signal, with the carrier frequency at the center frequency, and with the modulation being caused in large part from scatterer spacing and other tissue characteristics such as the presence of connective tissue around heart muscle bundles. The electrical return signal is demodulated and digitized (i.e., sampled) to form a demodulated and digitized return signal (DDRS). A variety of conventional techniques that are well known to persons skilled in the relevant arts may be used to form the DDRS. One example is to digitize the electrical return signal and then rectify the result (i.e., take the absolute value) to form a rectified digitized ultrasound return signal. Another example is to rectify the electrical return signal in analog form, and then digitize the result to form the DDRS. Alternative demodulation approaches may also be used to extract the modulation information from the electrical return signal, including but not limited to coherent demodulation, Hilbert transforms, and other demodulation techniques that are well known to persons skilled in the relevant arts.

Figure 13:
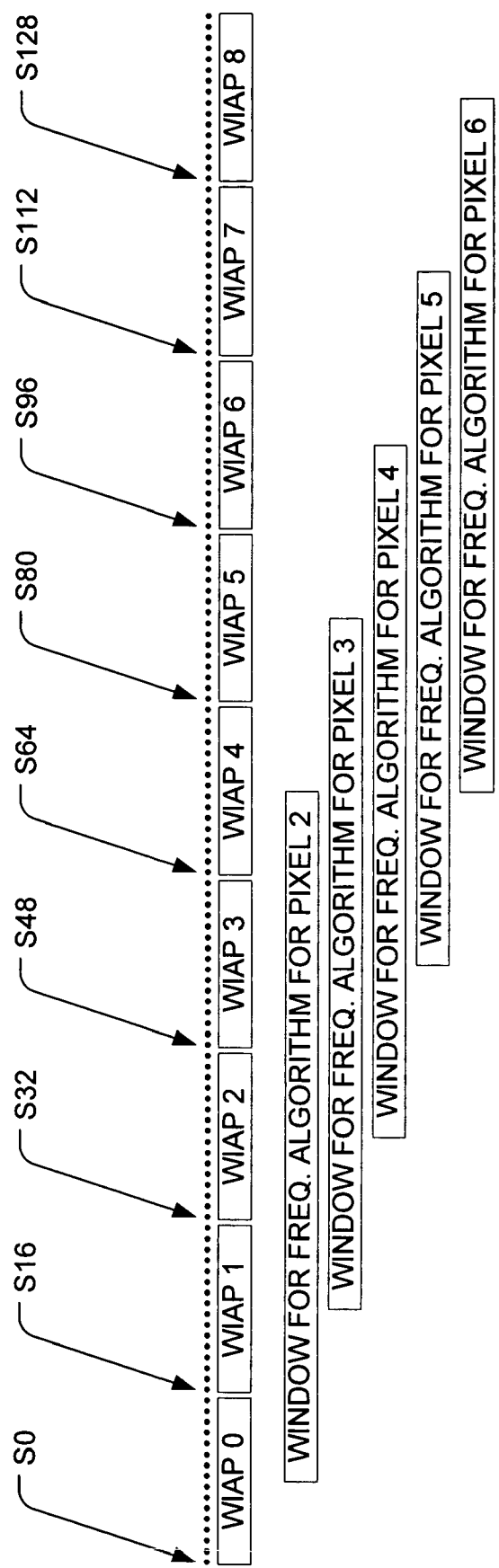
FIG. 13 is a schematic illustration of the samples that correspond to a section of one of the beams of FIG. 12.

FIG. 13 is a schematic illustration of the DDRS that corresponds to a section of one of the ultrasound beams $B_1 \ldots B_M$ of FIG. 12. Each sample is represented by a dot S0 ... S143. Each sample corresponds to a point in 2D space based on the direction of the beam and the time it took for the signal to travel from the transducer to the point in question and back. For example, if the return signal is digitized at 50 MHz, the time between samples will be 0.02 µs, which corresponds to a distance of 0.015 mm (based on the speed of sound in the body). Although the illustration only includes only 144 samples, an actual system would have many more samples in each scan line to provide the desired resolution. For example, to obtain a depth of penetration of 12 cm with the samples spaced 0.015 mm apart, 8000 samples would be needed. Because the beam of ultrasound energy is swept about a center point, polar coordinates are useful to organize the samples, at least in this stage of the processing. In some embodiments, the samples are analyzed entirely in polar coordinates, and only converted into rectangular coordinates for viewing on a conventional computer monitor. In other embodiments, the sample space may be converted into rectangular coordinates at an earlier stage of processing. The remaining explanation considers coordinates along each scan line (constant θ in the (r, θ) polar coordinate system, with r varying along the scan line), and pixel data associated with the center of the pixel along the scan line. Conversion to a sector image is well known in the field of ultrasound imaging.

The samples of each scan line are preferably processed by two different algorithms: one algorithm that analyzes intensity characteristics of the samples, and one algorithm that analyzes frequency characteristics of the samples.

For the first algorithm (i.e., the intensity algorithm) the samples of the scan line is divided into a plurality of pixels, with each pixel containing a plurality of samples. In the FIG. 13 example, each pixel contains 16 samples, as indicated by the boxes labeled "WIAP j" (which stands for "Window for Intensity Algorithm for Pixel j, where j is an integer from 0-8) that appear below the corresponding samples. Pixel data generated by signal processing is associated with the center position of the corresponding pixel. Of course, other numbers of samples per pixels could also be used instead of 16. In one preferred embodiment, for example, each pixel contains eight samples. The intensity algorithm is preferably a conventional image processing algorithm that converts the samples into a conventional image. The intensity for any given pixel is determined based on the amplitude of the samples that correspond to that pixel, with higher intensities corresponding to larger amplitudes. In the case of a 16 sample pixel, the average of those 16 samples would be used to determine the intensity at the pixel (with higher average intensity values appearing brighter and lower average intensity values appearing darker). Optionally, the intensity level of the pixel (or the samples that make up that pixel) may be compressed using conventional procedures such as logarithmic compression.

The second algorithm (i.e., the frequency algorithm) analyzes the frequency characteristics of the sample space and determines the spatial frequencies in scatterer spacing. Examples of suitable algorithms are described in U.S. Pat. No. 5,417,215 (hereinafter "the '215 patent"), which is incorporated herein by reference. The article "Spectral Analysis of Demodulated Ultrasound Returns: Detection of Scatterer Periodicity and Application to Tissue Classification" by S. Roth, H. M. Hastings, et al., published in Ultrasonic Imaging 19 (1997) at pp. 266-277, is also incorporated herein by reference.

The frequency algorithm provides a second result for each pixel in the image (i.e., in addition to the result produced by the intensity algorithm). Because most frequency analyzing algorithms provides better results when a larger number of data samples is used, and because each pixel only has a limited number of samples, samples on either side of the pixel in question are preferably combined with the samples in the pixel itself to increase the number of samples. In the illustrated example, each pixel contains 16 samples, but the frequency algorithm for any given pixel operates on 64 samples that are preferably centered in the pixel, as indicated by the boxes labeled "Window for Freq. Algorithm for Pixel k" (where k is an integer from 2-6) that appear below the samples. In this case, for example, all the samples from pixels 2-4 plus half the samples from pixels 1 and 5 would be used to perform the frequency analysis for pixel 3. Of course, other numbers of samples could be used for the frequency analysis instead of 64. Powers of 2, however, are preferable when a fast Fourier transform (FFT) algorithm is used. Optionally, windowing techniques (such as Hamming windows) may be used to weight the samples in the center more heavily than the samples that are near the ends.

Figure 14:
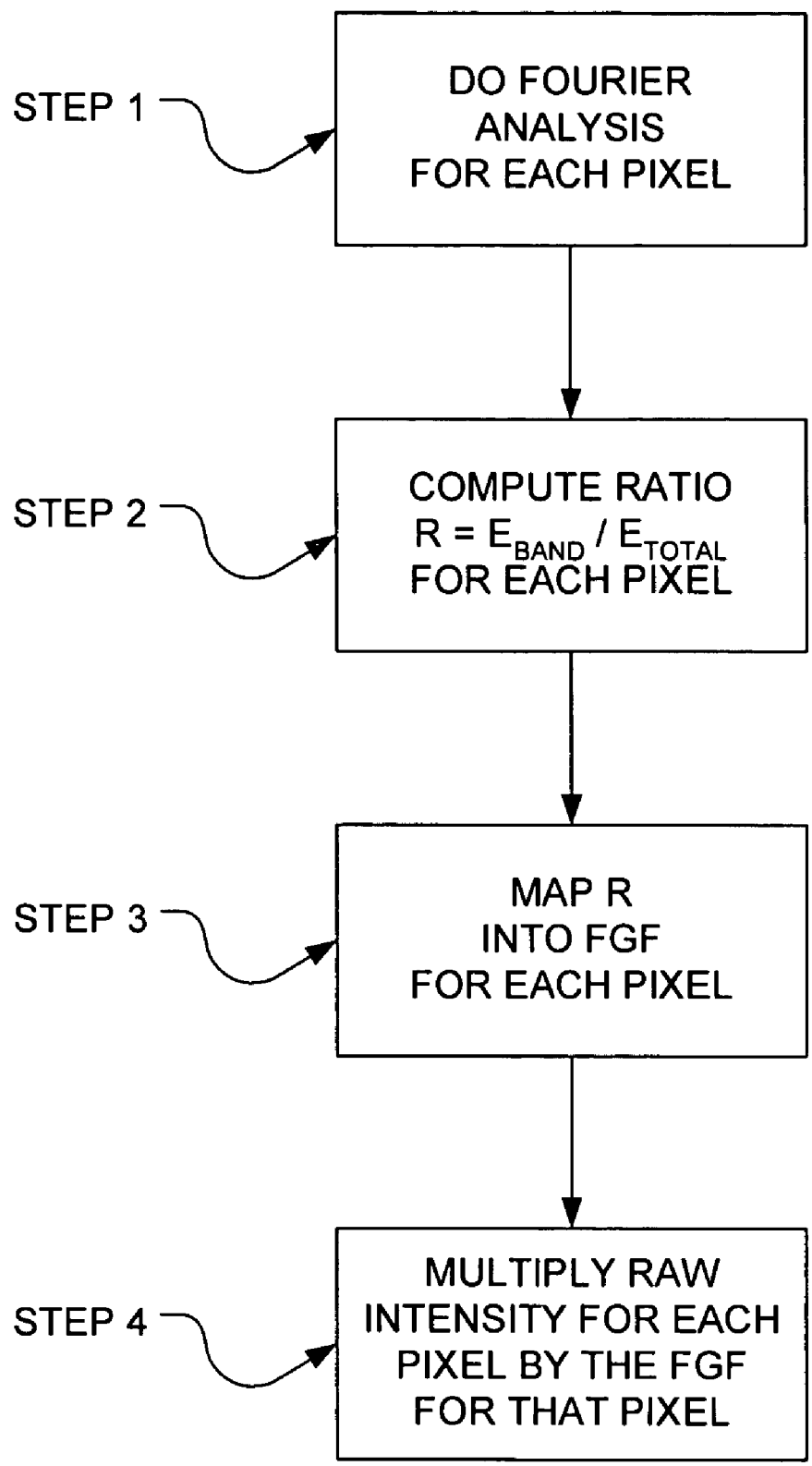
FIG. 14 is a flowchart of a processing algorithm that uses frequency characteristics of the return signal.

FIG. 14 is a flowchart of a suitable frequency algorithm. In this algorithm, steps 1 and 2, taken together, attempt to discern the material that the pixel in question is made of (and more specifically, whether that pixel is blood or muscle) based on the frequency characteristics of samples in the pixel and the samples in the neighboring pixels.

In step 1, a Fourier analysis is performed on the samples to determine the power distribution in the various frequency bands at each pixel. The end result of the Fourier analysis of step 1 is a set of amplitude coefficients for each of a plurality of different frequencies, for each of the pixels (i.e., one set of coefficients for the first pixel, a second set of coefficients for the second pixel, etc.). The Fourier analysis may be implemented using any of a variety of algorithms that are well known to persons skilled in the relevant arts (e.g., a conventional FFT algorithm). Alternative embodiments may use other frequency analysis tools to achieve similar results, such as bandpass techniques (preferably integer-based FIR recursive), wavelet techniques, etc. In step 2, the ratio of power in a selected frequency band to the power in the entire spectrum for each pixel is computed. Thus, for each pixel, the following formula applies:

$$R=E_{BAND}/E_{TOTAL}$$

Where $E_{BAND}$ is the power in the selected frequency band, $E_{TOTAL}$ is the total power in the portion of the spectrum, and R is the ratio of those two powers. When a Fourier analysis is used, the power in any given band equals the sum of the squares of the amplitudes of the Fourier coefficients within the band. The "selected frequency band" in this step is preferably selected so that changes in the ratio R are correlated to differences in the material that is being imaged (e.g., blood v. muscle). Alternatively, it may be selected so that changes in the ratio R are correlated to differences in S/N ratio, with larger Rs being correlated with signal and smaller Rs being correlated with speckle or electric noise. Optionally, different "selected frequency bands" may be used for near returns and for distant returns. For example, a wider frequency band may be used for signals that correspond to distant structures. In other words, the band selection can be a function of depth.

One suitable set of numeric values that results in a correlation between R and the material being imaged will now be discussed. Consider first the ultrasound return from a single scatter at a depth of r mm. The return from this scatter arrives after a time delay of t µs, given by $$t=r/v=r/(0.77 \text{ mm}/\mu s)=1.30 \text{ r } \mu s,$$

where the scaling factor of 0.77 mm/µs represents a round trip from the transducer to the scatterer and back (assuming the velocity of sound in tissue is to be 1.54 mm/µs).

The effects of scatterer periodicity upon the spectrum of the demodulated ultrasound return may be calculated in the case of separations large enough so that the ultrasound returns do not overlap (i.e., separations Δr larger than $\Delta r_0$=0.77 mm/µs×Δt). For example, in the case of an ideal one cycle pulse, a 5 MHz center frequency, and a ideal wide-bandwidth transducer, $$\Delta t=1/f_c=1/(5 \text{ MHz})=0.200 \text{ }\mu s,$$

and thus $$\Delta r_0=0.77 \text{ mm}/\mu s \times 0.200 \text{ }\mu s=0.154 \text{ mm}.$$

The internal structure of cardiac muscle displays variations on this and larger spatial scales. In contrast, scattering from blood is characterized by full-developed speckle, including variations on all, and especially much smaller spatial scales. As a result, low frequencies are indicative of muscle, and high frequencies are indicative of blood. This suggests defining the upper limit of a low frequency band to be less than about 4 MHz, corresponding to a minimal spatial scale $\Delta r_{MIN}$ of $$\Delta r_{MIN}=0.77\ mm/\mu s \times 1/(4\ MHz)=0.77\ mm/\mu s \times 250\ \mu s=0.193\ mm.$$

The inventors have performed tissue experiments that used a signal digitized at 50 MHz (corresponding to sampling interval of 0.02 μs), and computed the FFT in a 64 point window (corresponding to 64×0.02 μs=1.28 μs, or 0.986 mm). With that size window, the inventors selected a low frequency band that included Fourier frequencies of between 2 and 5 cycles per window (inclusive), which corresponds to frequencies between 2/1.28 MHz=1.56 MHz and 5/1.28 MHz=3.91 MHz.

Using the formula for R set forth above (R=$E_{BAND}/E_{TOTAL}$) for this low frequency band, the ratio of Fourier power in the low frequency band to the total Fourier power is computed for each pixel. The end result of step 2 in FIG. 14 is a value of R for each pixel.

The inventors have found that, for the parameter values used in this example, R-values of around 0.45 are significantly correlated to the presence of muscle tissue at the pixel of interest, and R-values of around 0.20 are significantly correlated to blood or regions dominated by electronic noise. The remaining part of the algorithm uses this information to improve the image by increasing the intensity of the portions of the image that correspond to muscle and decreasing the intensity of the portions of the image that correspond to blood. Since blood is less reflective than muscle, this difference enhances the contrast between blood and muscle.

The inventors have determined that cardiac ultrasound images are dramatically improved when the intensity of the areas with R-values corresponding to muscle is increased to about 120% of its original value, and when the intensity of the areas with R-values corresponding to blood is decreased to between about 20% and 50% of its original value. Thus, in step 3 of FIG. 14, a gain factor of about 1.2 is assigned to those portions of the image with R values of about 0.45, and a gain factor of between about 0.2 and 0.5 is assigned to those portions of the image with R values of about 0.20. This gain factor is referred to herein and a "feature gain factor" or FGF because the gain is feature dependant.

Figure 15:
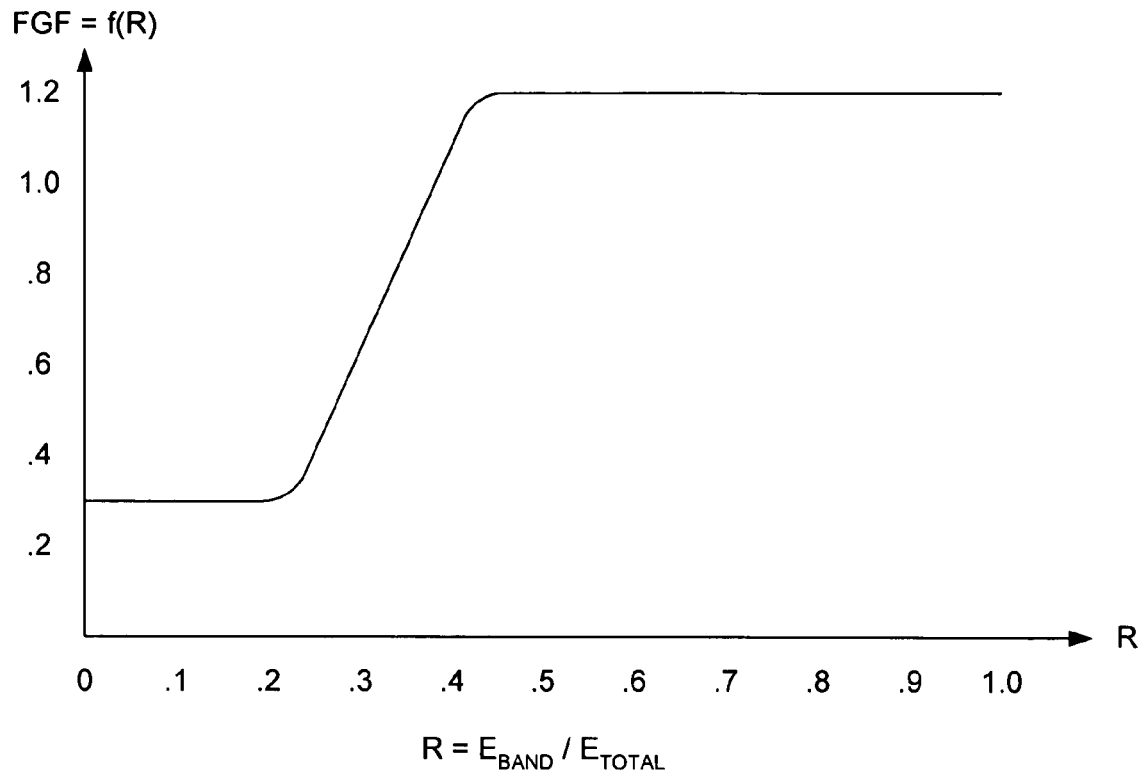
FIG. 15 is a graph of a function that maps a gain factor onto an energy ratio.

While most pixels in most images will have R-values that permit the pixel to be classified as being either muscle or blood, in some cases the classification is less clear. For example, pixels that straddle a boundary between muscle and blood have less predictable R values. In addition, although the R-values from blood may average out to 0.20, any given pixel of blood may vary widely from that R-value due to random statistical variations. Accordingly, a monotonic, preferably smooth function may be used to map R to FGF in some embodiments. FIG. 15 is an example of a suitable function for this purpose. Optionally, additional restrictions may be built into the mapping function, based on other tissue characteristics.

Finally, in step 4 of FIG. 14, the results of the intensity algorithm and the frequency algorithm are combined by multiplying the intensity value for each pixel (obtained from the intensity algorithm) by the FGF value for that pixel (obtained from the frequency algorithm). The result is an enhanced image in which the pixels that are probably muscle have been brightened while the pixels that are probably blood have been dimmed. This enhanced image is then displayed using conventional hardware and software techniques (including, for example, using interpolation to convert the polar coordinates to rectangular coordinates).

The actual choice of the Fourier frequency bands, R-values and corresponding FGF values depends upon a variety of factors including but not limited to transducer center frequency, sampling rate, window size and any optional windowing techniques used in signal processing, transducer bandwidth, the width of interrogating pulse, etc. In one embodiment, for example, a transducer center frequency of 7.5 MHz is used, the scan line is digitized at about four times the center frequency (i.e., about 30 MHz), and the distance between the samples is about 0.026 mm.

In alternative embodiments, other normalized (i.e., non-amplitude-dependent measures) may be used instead of dividing $E_{BAND}$ by $E_{TOTAL}$. For example, the ratio of power in a first frequency band to the power in a second frequency band may be used to compute R, as explained in the '215 patent (e.g., by dividing $E_{BAND1}$ by $E_{BAND2}$). In alternative embodiments, two or more Fourier analyses may be performed for each pixel, using a corresponding number of lines of samples, where the center of each line is contained within the pixel. For example, a two line per pixel arrangement in which a first 1D Fourier analyses is implemented along a line of samples in the radial direction, and a second 1D Fourier analyses is implemented along a second line of samples in the tangential direction. The results from those two lines of samples are then merged (e.g., by averaging). In still other embodiments, a 2D Fourier algorithm may be used instead of the 1D algorithms described above.

Ordinarily, the above-described operations are performed on the uncompressed image data. Under certain circumstances, however, it may be possible to perform corresponding operations directly on a compressed version of the image data.

Once the enhanced images have been generated, they may be displayed using conventional hardware. The images may be continuously updated and displayed for the entire time that the probe is in position, so that the physician can visualize the patient's heart in real time. In alternative embodiments, images may be acquired and optionally stored periodically (e.g., by capturing one or more complete heartbeats every two minutes). Optionally, the ability to compare a prior heartbeat to the current heartbeat may be provided by, for example, playing back a stored video clip (or "loop") of an old heartbeat in one window, and displaying the current image in a second window.

In contrast to conventional extended duration TEE using a transducer with a 10-15 mm azimuthal aperture, which is ordinarily done only under general anesthesia in the closely monitored environment of an room, the smaller diameter of the preferred embodiments described herein permits the preferred embodiments to be used without general anesthesia, and in less closely monitored environments. Optionally, the preferred embodiments may be used with sedation or local anesthesia in place of the general anesthesia that was used with conventional extended duration TEE. It may even be possible to forgo the use of sedation or anesthesia altogether. In such cases, the patient may optionally be medicated with an analgesic.

Optionally, regions of high relevance as detected by the feature gain factor may be highlighted, typically using colorization, while preserving the intensity of the gray-scale image, as explained in the '215 patent. Additional techniques for image enhancing can be found in U.S. Pat. No. 6,932,770, entitled "Method and Apparatus for Ultrasonic Imaging," which is incorporated herein by reference.

The preferred embodiments described above advantageously permit non-invasive, intermediate and long-term monitoring of cardiac function using a small transducer that fits into a housing approximately 5 mm in diameter, thereby reducing or eliminating the need for anesthesia. The preferred embodiments described above combine a plurality of techniques to produce images that are comparable to or better than images that were conventionally obtained by much larger transducers. The images produced by the preferred embodiments described above are repeatably and reliably usable for monitoring heart function, with adequate penetration depth to see the far wall of the left ventricle (10-12 cm) and adequate resolution to determine LV size and function from an image of the endocardial wall in real time, despite the use of a smaller transducer. Thus, in contrast to prior art systems which provide a depth of penetration that is less than 15 times the azimuthal aperture of the transducer (e.g., obtaining 10 cm penetration using a 10 mm transducer) the preferred embodiments can provide penetration that is greater than 15 times the azimuthal aperture of the transducer, or even greater than 20 times the azimuthal aperture of the transducer (e.g., obtaining 10 cm penetration using a 4.75 mm transducer).

The preferred embodiments described above use a probe that is much narrower than conventional TEE probes, and may be used to monitor heart function over an extended period of time and to obtain an understanding of the patients' hemodynamic status. Such information may be useful in choosing treatments and improving outcome in many situations (including but not limited to critical medical problems such as hypotension, pulmonary edema and heart failure).

The above-described embodiments permit direct visualization of cardiac function, which permits evaluation of a patient's hemodynamic status including intravascular volume (normal, low or high), cardiac contractility (how well the left ventricle pumps), cardiac ischemia (inadequacy of blood flow to the heart muscle) and cardiac tamponade (fluid in the pericardial sac limiting heart function). For example, information about intravascular volume status can be derived from directly visualizing the size of the left ventricle and monitoring changes in size with treatments over time. Information about contractility can be obtained by directly visualizing the contraction (pumping) of the left ventricle, either using qualitative visual estimates or quantitatively. Information about ischemia is available during direct visualization of the left ventricle since ischemia results in abnormal motion of the walls of the left ventricle (wall motion abnormality). Information about possible cardiac tamponade or pericardial effusion (fluid in the heart sac) is available when using ultrasound to directly visualize the heart.

The narrowness of the probe may enable the above-described embodiments to provide this information for longer periods of time, outside the operating room, and/or without anesthesia. The above-described embodiments also lend themselves to use in settings where interventional cardiac procedures are performed such as the cardiac catheterization and electrophysiology laboratories, both for monitoring the effects of physicians' interventions on cardiac and hemodynamic function and for guiding the placement of devices. For example, they may be used to help the physician correctly place the pacing leads to achieve the desired result. The above-described embodiments may also be used in non-cardiac applications in which a narrower probe is needed or beneficial.

The above-described embodiments are not limited to ultrasound imaging modes, and may be used in alternative ultrasound modes (e.g., pulsed wave Doppler, continuous wave Doppler, and color flow imaging Doppler modes). These alternative modes may be performed using the same transducer as the above-described imaging modes and may yield information which can be combined with images, optionally in real-time. For example, color flow Doppler information may be obtained during imaging of the mitral valve (between the left atrium and left ventricle) while maintaining transducer position in the mid to lower esophagus. Such an application would permit evaluation of leakage of the mitral valve (mitral regurgitation or insufficiency).

If desired, the preferred embodiments described above may be scaled down for neonatal or pediatric use. In such cases, a transducer that is between about 2.5 and 4 mm in the azimuthal direction is preferable, with the elevation dimension scaled down proportionally. Because less depth of penetration is required for neonatal and pediatric patients, the operating frequency may be increased. This makes $\lambda$ smaller, which permits the use of a smaller transducer element spacing (pitch), and a correspondingly larger number of elements per mm in the transducer. When such a transducer is combined with the above-described techniques, the performance should meet or surpass the performance of conventional 7.5 mm TEE probes for neonatal and pediatric uses.

The embodiments described herein may also be used in non-cardiac applications. For example, the probe could be inserted into the esophagus to monitor the esophagus itself, lymph nodes, lungs, the aorta, or other anatomy of the patient. Alternatively, the probe could be inserted into another orifice (or even an incision) to monitor other portions of a patient's anatomy.

If desired, the center frequency may be lowered (e.g., down to about 4.5 MHz) to provide additional depth of penetration when needed (e.g., for very large patients). Although this will also reduce the resolution, the result may be acceptable when very large structures are being imaged. Alternatively, the transducer size and housing diameter may be scaled up in size (e.g., to about 7 mm) if the reduced resolution results in unusable images.

Numerous alternative and optional features may be substituted and added to the above-described embodiment. One optional feature is digital beamforming using significant oversampling. For example, if the transducer is operated at 7 MHz, and the return is digitized at 30× frequency, 30×7 MHz=210 MHz digitization would be required. That data could then be downsampled by a factor of five to reduce the number of data points to a 42 MHz sample. Such downsampling would reduce the noise floor due to front-end noise by a factor of $\sqrt{5}$, (i.e., over 2 bits in power). Similarly, downsampling by a factor of 7 would reduce the noise floor by a factor of $\sqrt{7}$.

Figure 16A:
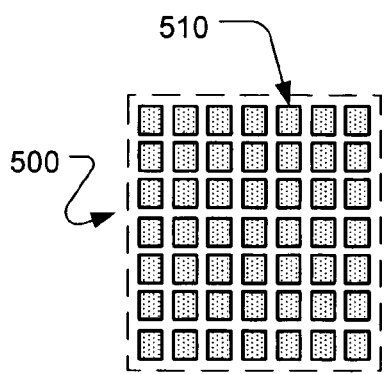
FIGS. 16A and 16B show two alternative transducer designs.

FIG. 16A depicts the front face of an alternative 2D transducer 500, which includes a 2D array of active elements 510. The concepts described herein can also be implemented using this type of transducer by making appropriate adjustments that will be apparent to persons skilled in the relevant arts.

Figure 16B:
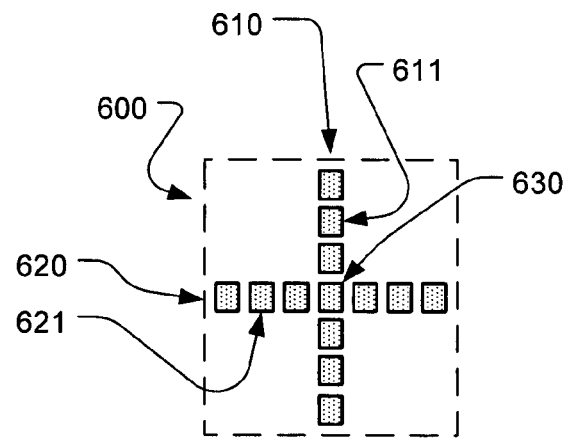

FIG. 16B depicts the front face of another alternative 2D transducer design that is referred to as a "sparse 2D transducer." The sparse 2D transducer 600 has a column 610 of "transmit" elements 611, used for transmitting the ultrasound, and a row 620 of receive elements 621 used for receiving the ultrasound signal. As shown, there is one element 630 common to both the column 610 of transmit elements and the row 620 of receive elements. This common element 630 may be used for transmission, reception, or both. This transducer design reduces electronic noise by using separate transmit and receive elements, which eliminates the need for electronic transmit/receive switches at the elements. The concepts described herein can also be implemented using this type of transducer by making appropriate adjustments that will be apparent to persons skilled in the relevant arts.

Alternative embodiments of the invention may use fewer techniques and/or implement those techniques to a lesser extent, and still maintain the ability to produce an acceptable image. For example, depending on the other components in the system, it may be possible to obtain an acceptable image using a 75° sector width, or even using a 90° sector width. It may also be possible to obtain an acceptable image using a transducer with an elevation:transverse aspect ratio of about 2:3 in place of the preferred 1:1 or 2:1 aspect ratios. Another alternative would be to use some or all of the above-described techniques with a transducer that is slightly larger than the preferred embodiments described above, yet still smaller than conventional 10 mm TEE transducer. Numerous other modifications to the above-described embodiments will be apparent to those skilled in the art, and are also included within the purview of the invention.

We claim:

1. An ultrasound imaging system that interfaces with an ultrasound transducer, the system comprising:
    an ultrasound frequency transmitter that generates drive signals for the ultrasound transducer for each line of an image;
    a ultrasound frequency receiver that receives return signals from the ultrasound transducer and outputs samples of the received return signals for each line of the image; and
    an image processor that processes pixels of the image by performing the steps of (a) computing a ratio of power in a predetermined spatial frequency band to total power for samples of the received return signal that are associated with a given pixel, wherein the samples have a first linear density and the pixels have a second linear density, and the first linear density is at least twice as high as the second linear density, (b) mapping the computed ratio to a gain for the given pixel, and (c) modifying a raw intensity of the given pixel in accordance with the gain,
    wherein the raw intensity for the given pixel is determined by averaging a group of J samples centered about the given pixel, and wherein the step of computing a ratio comprises determining frequency characteristics of a group of K samples centered about the given pixel, where K is greater than J.

2. The system of claim 1, wherein the predetermined frequency band is a low frequency band.

3. The system of claim 1, wherein the upper bound of the predetermined frequency band is about 4 MHz.

4. The system of claim 1, wherein the upper bound of the predetermined frequency band is about 4 MHz and the lower bound of the predetermined frequency band is about 1.5 MHz.

5. The system of claim 1, wherein the step of computing a ratio comprises determining frequency characteristics of a group of samples centered about the given pixel.

6. The system of claim 1, wherein the step of computing a ratio comprises determining frequency characteristics of a group of samples centered about the given pixel using a Fast Fourier Transform algorithm.

7. The system of claim 1, wherein the raw intensity for the given pixel is determined by averaging a group of samples centered about the given pixel.

8. The system of claim 1, further comprising a probe including (a) a housing having a distal end, (b) an ultrasound transducer mounted in the distal end of the housing, and (c) an interface that operatively connects the ultrasound transducer to the transmitter and the receiver, wherein the transducer is transversely oriented.

9. The system of claim 1, further comprising a probe including (a) a housing having a distal end, (b) an ultrasound transducer mounted in the distal end of the housing, and (c) an interface that operatively connects the ultrasound transducer to the transmitter and the receiver, wherein the transducer is a transversely oriented phased-array transducer with a size in an elevation direction of at least about 6 mm and wherein a ratio of the size of the transducer in the elevation direction to the size of the transducer in an azimuthal direction is at least about 1.5:1.

10. The system of claim 1, wherein the step of computing a ratio comprises the steps of: determining frequency characteristics of a group of samples centered about the given pixel using a Fast Fourier Transform algorithm; and dividing a sum of the squares of all Fourier coefficients in a first band by the sum of the squares of all Fourier coefficients.

11. The system of claim 1, wherein the first linear density is 8 times as high as the second linear density.

12. The system of claim 1, wherein the first linear density is 16 times as high as the second linear density.

13. A method for processing ultrasound images that include at least two types of tissue, the method comprising the steps of:
    computing, in a processor, a ratio of power in a predetermined spatial frequency band to total power for a plurality of samples of a received return signal that are associated with a given pixel, wherein the samples have a first linear density and the pixels have a second linear density, and the first linear density is at least twice as high as the second linear density;
    mapping, in the processor, the computed ratio to a gain for the given pixel;
    modifying, in the processor, a raw intensity of the given pixel in accordance with the gain; and
    displaying the pixel with the modified intensity,
    wherein the raw intensity for the given pixel is determined by averaging a group of J samples centered about the given pixel, and wherein the step of computing a ratio comprises determining frequency characteristics of a group of K samples centered about the given pixel, where K is greater than J, and
    wherein the received return signal is an ultrasound return signal produced by an ultrasound transducer.

14. The method of claim 13, wherein the predetermined frequency band is a low frequency band.

15. The method of claim 13, wherein the upper bound of the predetermined frequency band is about 4 MHz.

16. The method of claim 13, wherein the upper bound of the predetermined frequency band is about 4 MHz and the lower bound of the predetermined frequency band is about 1.5 MHz.

17. The method of claim 13, wherein the step of computing a ratio comprises determining frequency characteristics of a group of samples centered about the given pixel.

18. The method of claim 13, wherein the step of computing a ratio comprises determining frequency characteristics of a group of samples centered about the given pixel using a Fast Fourier Transform algorithm.

19. The method of claim 13, wherein the raw intensity for the given pixel is determined by averaging a group of samples centered about the given pixel.

20. The method of claim 13, wherein the first linear density is 8 times as high as the second linear density.

21. The method of claim 13, wherein the first linear density is 16 times as high as the second linear density.

22. An ultrasound imaging system that interfaces with an ultrasound transducer, the system comprising:

an ultrasound frequency transmitter that generates drive signals for the ultrasound transducer for each line of an image;

a ultrasound frequency receiver that receives return signals from the ultrasound transducer and outputs samples of the received return signals for each line of the image; and an image processor that processes pixels of the image by performing the steps of (a) computing a ratio of power in a first spatial frequency band to power in a second spatial frequency band for samples of the received return signal that are associated with a given pixel, wherein the samples have a first linear density and the pixels have a second linear density, and the first linear density is at least twice as high as the second linear density, (b) mapping the computed ratio to a gain for the given pixel, and (c) modifying a raw intensity of the given pixel in accordance with the gain, wherein the raw intensity for the given pixel is determined by averaging a group of J samples centered about the given pixel, and wherein the step of computing a ratio comprises determining frequency characteristics of a group of K samples centered about the given pixel, where K is greater than J.

23. The system of claim 22, wherein the first frequency band is a low frequency band.

24. The system of claim 22, wherein the first frequency band is a low frequency band and the second frequency band includes all frequencies.

25. The system of claim 22, wherein the step of computing a ratio comprises the steps of: determining frequency characteristics of a group of samples centered about the given pixel using a Fast Fourier Transform algorithm; and dividing a sum of the squares of all Fourier coefficients in a first band by a sum of the squares of all Fourier coefficients in the second band.

26. The system of claim 22, further comprising a probe including (a) a housing having a distal end, (b) an ultrasound transducer mounted in the distal end of the housing, and (c) an interface that operatively connects the ultrasound transducer to the transmitter and the receiver, wherein the transducer is transversely oriented.

27. The system of claim 22, further comprising a probe including (a) a housing having a distal end, (b) an ultrasound transducer mounted in the distal end of the housing, and (c) an interface that operatively connects the ultrasound transducer to the transmitter and the receiver, wherein the transducer is a transversely oriented phased-array transducer with a size in an elevation direction of at least about 6 mm and wherein a ratio of the size of the transducer in the elevation direction to the size of the transducer in an azimuthal direction is at least about 1.5:1.

28. The system of claim 22, wherein the first linear density is 8 times as high as the second linear density.

29. The system of claim 22, wherein the first linear density is 16 times as high as the second linear density.

30. A method for processing ultrasound images that include at least two types of tissue, the method comprising the steps of:

computing, in a processor, a ratio of power in a first spatial frequency band to power in a second spatial frequency band for a plurality of samples of a received return signal that are associated with a given pixel, wherein the samples have a first linear density and the pixels have a second linear density, and the first linear density is at least twice as high as the second linear density;

mapping, in the processor, the computed ratio to a gain for the given pixel;

modifying, in the processor, a raw intensity of the given pixel in accordance with the gain; and displaying the pixel with the modified intensity, wherein the raw intensity for the given pixel is determined by averaging a group of J samples centered about the given pixel, and wherein the step of computing a ratio comprises determining frequency characteristics of a group of K samples centered about the given pixel, where K is greater than J, and wherein the received return signal is an ultrasound return signal produced by an ultrasound transducer.

31. The method of claim 30, wherein the first frequency band is a low frequency band.

32. The method of claim 30, wherein the first frequency band is a low frequency band and the second frequency band includes all frequencies.

33. The method of claim 30, wherein the step of computing a ratio comprises the steps of: determining frequency characteristics of a group of samples centered about the given pixel using a Fast Fourier Transform algorithm; and dividing the sum of the squares of the Fourier coefficients in the first band by the sum of the squares of the Fourier coefficients in the second band.

34. The method of claim 30, wherein the step of computing a ratio comprises the steps of: determining frequency characteristics of a group of samples centered about the given pixel using a Fast Fourier Transform algorithm; and dividing the sum of the squares of the Fourier coefficients in the first band by the sum of the squares of all the Fourier coefficients.

35. The method of claim 30, wherein the first linear density is 8 times as high as the second linear density.

36. The method of claim 30, wherein the first linear density is 16 times as high as the second linear density.

* * * * *